(12) United States Patent
Groutas

(10) Patent No.: US 6,495,358 B1
(45) Date of Patent: Dec. 17, 2002

(54) SULFAMIDE AND BIS-SULFAMIDE AMINO ACID DERIVATIVES AS INHIBITORS OF PROTEOLYTIC ENZYMES

(75) Inventor: William C. Groutas, Wichita, KS (US)

(73) Assignee: Wichita State University, Wichita, KS (US)

( * ) Notice: Subject to any disclaimer, the term of this patent is extended or adjusted under 35 U.S.C. 154(b) by 0 days.

(21) Appl. No.: 09/552,554

(22) Filed: Apr. 19, 2000

(51) Int. Cl.$^7$ .............................. C12N 9/48; C12N 9/50; A01N 41/06; A61K 31/18

(52) U.S. Cl. ........................ 435/212; 435/219; 514/600; 514/601; 514/605

(58) Field of Search ................................ 514/600, 601, 514/605; 435/184, 212, 219

(56) References Cited

U.S. PATENT DOCUMENTS

| | | | |
|---|---|---|---|
| 5,455,258 A | 10/1995 | MacPherson et al. | 514/357 |
| 5,539,102 A | 7/1996 | Sendo et al. | 540/310 |
| 5,550,139 A | 8/1996 | Groutas et al. | 514/362 |
| 5,602,119 A | * 2/1997 | Vazquez et al. | |
| 5,723,490 A | 3/1998 | Tung | 514/478 |
| 5,756,498 A | * 5/1998 | Vazquez et al. | |
| 5,783,701 A | * 7/1998 | Tung et al. | |

FOREIGN PATENT DOCUMENTS

| | | |
|---|---|---|
| WO | WO-9410134 A1 * | 5/1994 |
| WO | WO 95/35275 | 12/1995 |
| WO | WO 96/00214 | 1/1996 |

OTHER PUBLICATIONS

Supuran et al., "Protease Inhibitors. Synthesis of L–Alanine Hydroxamate Sulfonyated Derivatives as Inhibitors of Clostridium histolyticum Collagenase" (2000b) J. Enz. Inhib., 15(2), 111–128.*

Bailey et al., "A Structural Comparison of 21 Inhibitor Complexes of the Aspartic Proteinase from *Endothia parasitica*" (1994) Prot. Sci., 3(11), 2129–2143.*

Lunney et al., "Analyses of Ligand Binding in Five Endothiapepsin Crystal Complexes and Their Use in the Design and Evaluation of Novel Renin Inhibitors" (1993) J. Med. Chem., 36(24), 3809–3820.*

Kempf et al., "Symmetry–Based Inhibitors of HIV Protease. Structure–Actvity Studies of Acylated 2,4–Diamino–1, 5–diphenyl–3–hydroxypentane and 2,5–Diamino–1, 6–diphenylhexane–3,4–diol" (1993) J. Med. Chem., 36(3), 320–330.*

Betz, A., et al., "Inhibition of Faxtor Xa by a Peptidyl–α–ketothiazole Involves Two Steps. Evidence for a Stabilizing Conformational Change" *Biochemistry* vol. 38 No. 44:14582–14591 (1999).

Bulychev A., et al., "Potent Mechanism–Based Inhibition of the TEM–1 β–Lactamse by Novel N–Sulfonyloxy β–Lactams" *J. Am. Chem. Soc.* vol. 117 No. 22:5938–5943 (1995).

Dragovich, P.S. et al., "Structure–Based Design of Ketone–Containing, Tripeptidyl Human Rhinovirus 3C Protease Inhibitors" *Bioorg. Med. Chem. Lett.* vol. 10:45–48 (2000).

Groutas, W.C., et al., "$^{13}$C NMR Evidence for an Enzyme–Induced Lossen Rearrangement in the Mechanism–Based Inactivation of α–Chymotrypsin by 3–Benzyl–N–((methylsulfonyl)oxy)succimide" *J. Am. Chem. Soc.* vol. 111:1932–1933 (1989).

Groutas, W.C. et al., "Inhibition of Human Leukocyte Elastase by Derivatives of N–Hydroxysuccinimide. A Structure–Activity–Relationship Study" *J. Med. Chem.* vol. 32:16071611 (1989).

(List continued on next page.)

*Primary Examiner*—Jon P. Weber
(74) *Attorney, Agent, or Firm*—Clark & Elbing LLP

(57) ABSTRACT

Compounds of the general formula I are provided:

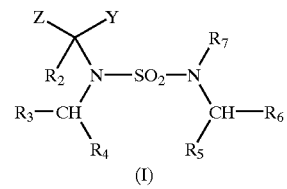

(I)

and pharmaceutically acceptable salts thereof, wherein,

Z is a chemical species or $R_i$ capable of binding at a primary specificity site of a protease;

Y is a chemical species reactive to a specific class of protease;

each of $R_2$, $R_3$, $R_5$ and $R_7$ is independently selected from the group consisting hydrogen, alkyls, aryls, substituted aryls, alkylaryls and arylalkyls;

$R_4$ and $R_6$ are independently selected from the group consisting of:
  (a) H, alkyl, aryl, arylalkyl, alkylaryl, substituted derivatives thereof, and $R_i$;
  (b) —C(O)OH and derivatives thereof, said derivatives selected from the group consisting of —C(O)OQ, —C(O)NR$_Y$R$_Z$, —C(O)[NHCHR$_{i(q)}$C(O)]$_q$OQ, and —C(O)[NHCHR$_{i(q)}$C(O)]$_q$NR$_Y$R$_Z$; and
  (c) —CHR$_i$NH$_2$ and derivatives thereof, said derivatives selected from the group consisting of —CHR$_i$NHW, —CHR$_i$NHC(O)OQ, —CHR$_i$NHC(O)R, —CHR$_i$NHC(O)NR$_Y$R$_Z$, —CHR$_i$NHC(O)[NHCHR$_{i(q)}$C(O)]$_q$OQ, —CHR$_i$NHSO$_2$R, and —CHR$_i$NH[C(O)CHR$_{i(r)}$NH]$_r$W, where q and r independently are integers from 1 to 10 inclusive; J is a carboxyl protecting group; G is an amino protecting group; Q is H, R or J; W is H, R or G; each $R_i$ is independently selected from naturally or non-naturally occurring amino acid side chains; R is alkyl, aryl, substituted aryl, alkylaryl, arylalkyl, or heterocyclic radical; and each $R_Y$ and $R_Z$ is independently H, alkyl, aryl, substituted aryl, alkylaryl, arylalkyl, or heterocyclic radical.

30 Claims, 12 Drawing Sheets

OTHER PUBLICATIONS

Groutas, W.C. et al., "Hydantoin Derivatives. A New Class of Inhibitors of Human Leukocyte Elastase" *J. Enzyme Inhibition* vol. 3:237–243 (1990).

Groutas, W.C. et al., "Potential Mechanism–Based Inhibitors of Proteolytic Enzymes" *Bioorg. Med. Chem. Lett.* vol. 2 No. 2:175–180 (1992).

Groutas, W.C. et al., "Inhibitors of Human Neutrophil Cathepsin G: Structural and Biochemical Studies" *Archives Biochem. Biophys.* vol. 294 No. 1:144–146 (Apr. 1992).

Groutas, W.C. et al., "Efficient Inhibition of Human Leukocyte Elastase and Cathepsin G by Saccharin Derivatives" *J. Med. Chem.* vol. 36 No. 21:3178–3181 (1993).

Groutas, W.C. et al., "Mechanism–Based Inhibitors of Serine Proteinases Based on the Gabriel–Colman Rearrangement" *Biochemical and Biophysical Research Communications* vol. 194 No. 3:1491–1499 (Aug. 1993).

Groutas, W.C. et al., "Dual Action Inhibitors of Proteolytic Enzymes: Potential Therapeutic Agents for Cyctic Fibrosis and Related Ailments" *Bioorganic & Medicinal Chemistry* vol. 1 No. 4:273–277 (1993).

Groutas, W.C. et al., "Novel Potential Mechanism–Based Inhibitors of Human Leukocyte Elastase and Cathepsin G: Derivatives of Isothiazolidin–3–one" *Biochem. Biophys. Research Comm.* vol. 197 No. 2:730–739 (Dec. 1993).

Groutas, W.C. et al., "Substituted 3–Oxo–1,2,5–thadiazolidine 1,1 Dioxides: A New Class of Potential Mechanism–Based Inhibitors of Human Leukocyte Elastase and Cathepsin G" *Biochem. Biophys. Research Comm.* vol. 198: 341–349 (1994).

Huang, Y. et al., "Synthesis and Testing of Azaglutamine Derivatives as Inhibitors of Hepatitis A Virus (HAV) 3C Proteinase" *Bioorg. Med. Chem.* vol. 7:607–619 (1999).

Kuang, R. et al., "A General Inhibitor Scaffold for Serine Proteases with a (Chymo)trypsin–Like Fold: Solution–Phase Construction and Evaluation of the First Series of Libraries of Mechanism–Based Inhibitors" *J. Am. Chem. Soc.* vol. 121 No. 35:8128–8129 (1999).

Morphy, J.R. et al., "Matrix Metalloproteinase Inhibitors: Current Status" *Current Med. Chem.* vol. 2 No. 3:743–762 (1995).

Pikul, S. et al., "Discovery of Potent, Achiral Matrix Metalloproteinase Inhibitors" *J. Med. Chem.* vol. 41 No. 19:3568–2571 (1998).

Pinto, I.L. et al., "Novel, Selective Mechanism–Based Inhibitors of the Herpes Proteases" *Bioorg. Med. Chem. Lett.* vol. 6 No. 20:2467–2472 (1996).

Scozzafava et al., "Protease Inhibitors—Part 5. Alkyl/Arylsulfonyl– and Arylsufonylureido–/Arylureido– Glycine Hydroxamate Inhibitors of Clostridium histolyticum Collagenase" (2000a) Eur. J. Med. Chem., 35(3), 299–307.*

Scozzafava et al., "Protease Inhibitors. Part 8. Synthesis of Potent Clostridium histolyticum Collagenase Inhibitors Incorporating Sulfonylated L–Alanine Hydroxamate Moieties" (2000b) Bioorg. Med. Chem., 8(3), 637–645.*

Scozzafava et al., "Protease Inhibitors. Synthesis of Clostridium histolyticum Collagenase Inhibitors Incorporating Sulfonyl–L– Alanine Hydroxamate Moieties" (2000c) Bioorg. Med. Chem. Lett., 10(5), 499–502.*

Supuran et al., "Protease Inhibitors. Part 7 Inhibition of Clostridium histolyticum Collagenase with Sulfonyated Derivatives of L–Valine Hydroxamate" (2000a) Eur. J. Pharm. Sci., 10(1), 67–76.*

* cited by examiner (serine protease inhibitors)

(cysteine inhibitors)

(X=COOEt, $SO_2$Ph, etc)

[a] $Ph_3P$=CHCOOEt
[b] $Ph_3P$=CH$SO_2$Ph (MMP inhibitors)

$^a$ClSO$_2$NHCOOBzl/TEA; $^b$NaH then ClSO$_2$NHCOOBzl; $^c$LiBH$_4$
$^d$(ClCO)$_2$/DMSO/TEA; $^e$BrCF$_2$COOEt/Zn; $^f$(CH$_3$)$_3$SiI; $^g$ClCOOR
RCOOH/CDI or RN=C=O; $^h$2-Thiazole/n-BuLi Scheme 5 Synthesis of Inhibitor 15

$^a$ CDI/HN(CH$_3$)OCH$_3$/TEA; $^b$ TFA/CH$_2$Cl$_2$
$^c$ ClSO$_2$N(CH$_3$)$_2$/TEA/DMAP; $^d$ PhCH$_2$Br/NaH
$^e$ LiAlH$_4$ / ether Scheme 2 Synthesis of MMP Inhibitors 20 & 30

R = H 20
isopropyl 30

$^a$ClSO$_2$N(CH$_3$)$_2$/TEA/DMAP; $^b$NaH/PhCH$_2$Br;
$^c$NH$_2$OH (HCl) / KOH/EtOH

Dixon plot for the inhibition of human leukocyte elastase by compound 15

(Sulfamide derivatives with N-protected Amino Acids at the R$_4$ site)

$^a$(L) Z-prolinal/NaBH (OAc)$_3$; $^b$ClSO$_2$NHCOOt-Bu/TEA; $^c$ TFA
$^d$H$_2$/Pd-C; $^e$IBCF/ (L) Z-Val; $^f$LiBH$_4$; $^g$HOOCCH$_2$CH$_2$Ph/ CDI;
$^h$(ClCO)$_2$/DMSO/TEA; $^i$Zn/BrCF$_2$COOEt Sulfamide Derivatives with N-protected
Amino Acids at the $R_6$ Site $^a$ PhCHO/NaBH(OAc)$_3$ ; $^b$ ClSO$_2$NHCOOt-Bu; $^c$ CF$_3$COOH;
$^d$ LiBH$_4$ ; $^e$ O=C=N(CHPh)COOt-Bu; $^f$ IBCF/ (L) Ala-OCH$_3$ ;
$^g$(ClCO)$_2$/DMSO/TEA; $^h$BrCF$_2$COOEt/Zn <sup>a</sup> PhCHO/NaBH(OAc)$_3$ ; <sup>b</sup> ClSO$_2$N=C=O/t-BuOH/TEA <sup>c</sup> CF$_3$COOH; <sup>d</sup> NH$_2$OH (HCl) / KOH/EtOH; <sup>e</sup> ClCOOCH$_2$Ph/TEA

SULFAMIDE AND BIS-SULFAMIDE AMINO ACID DERIVATIVES AS INHIBITORS OF PROTEOLYTIC ENZYMES

STATEMENT AS TO FEDERALLY SPONSORED RESEARCH

This invention was made with the support of the United States government under National Institutes of Health Grant No. 57788. The United States may have certain rights in the invention.

BACKGROUND OF THE INVENTION

The invention relates to acyclic sulfamides and bis-sulfamides useful as inhibitors of proteolytic enzymes. The invention further relates to general templates for use in designing combinatorial libraries, screening and identification of biologically active, peptidomimetic protease inhibitors. There are four classes of proteases: serine, cysteine, aspartic and metalloproteases.

Degenerative diseases associated with serine proteases such as human leukocyte elastase (HLE) include cystic fibrosis, chronic obstructive pulmonary disease (e.g., emphysema and asthma), adult respiratory distress syndrome (ARDS), inflammatory bowel disease, chronic bronchitis, psoriasis, rheumatoid arthritis, pancreatitis, periodontal disease, and other inflammatory diseases A variety of cyclic mechanism-based inhibitors of serine proteases are known. Exemplary protease inhibitors include sulfonyloxy derivatives of isothiazolidin-3-one 1,1-dioxides (Groutas et al., *Biochemical and Biophysical Research Communications* 1997(2):730 (December, 1993)), 1,2,5-thiadiazolidin-3-one 1,1-dioxides (Kuang et al., *J. Am. Chem. Soc.* 121:8128 (September 1999)) and 3-alkyl-N-hydroxysuccinimides (Groutas et al., *J. Med. Chem.* 32:1607 (1989)). These compounds react irreversibly with a variety of serine proteases via a sequence of steps involving binding of the inhibitor molecule to the active site of the enzyme, nucleophilic ring opening of the cyclic inhibitor, rearrangement of the ring-opened structure to provide a reactive intermediate, followed by irreversible reaction of the compound with a second site on the enzyme, resulting in enzyme deactivation.

Diseases associated with cysteine proteases include cancer metastasis, osteoporosis and osteoarthritis (McGrath et al. *Nature: Structural Biology* 4(2):105 (1997)), bone resorption, muscular dystrophy, parasitic diseases (leishmaniasis, malaria) (Li et al. *Bioorg. Med. Chem.* 4(9):1421 (1996); Rosenthal et al. *J. Clin. Invest.* 91:1052 (1993)), inflammation, common cold (Webber et al. *J. Med. Chem.* 39:5072 (1996)), and hepatitis A (Malcolm et al. *Biochemistry* 34:8172 (1996)). Many known cysteine protease inhibitors are peptidyl aldehydes, halomethylketones and Michael acceptors (α,β-unsaturated groups).

Matrix metalloproteinases (MMPs), such as collagenase, stromelysin and gelatinase, are involved in connective tissue breakdown. Metalloproteinase (MMP) inhibitors are of potential value in the treatment of neuroinflammatory disorders, including those involving myelin degradation, for example, multiple sclerosis, as well as management of angiogenesis-dependent diseases, proliferative retinopathies, neovascular glaucoma, ocular tumors, angiofibromas and hemangiomas. See, WO 95/35275, entitled "Metalloproteinase Inhibitors". Many known metalloproteinases are characterized by the presence in the structure of a zinc(II) ion at the active site, and thus, most known MMP inhibitors typically include hydroxamic acid or carboxylic acid to bind zinc. For example, arylsulfonamide-substituted hydroxamic acids have been reported as matrix metalloproteinase inhibitors. See, U.S. Pat. No. 5,455,258 to MacPherson et al.

SUMMARY OF THE INVENTION

The present invention makes available a new class of compounds useful as protease inhibitors. The open sulfamide structure is anticipated to be more stable chemically than related closed ring structures, e.g., 1,2,5-thiadiazolidin-3-one 1,1-dioxides, yet show high inhibition of proteolytic activity.

The invention features a compound having the general formula I

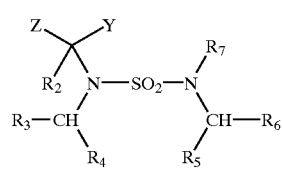

and pharmaceutically acceptable salts thereof, wherein,

Z is a chemical species or $R_1$ capable of binding at a primary specificity site of a protease;

Y is a chemical species reactive to a specific class of protease;

each of $R_2$, $R_3$, $R_5$ and $R_7$ is independently selected from the group consisting hydrogen, alkyls, aryls, substituted aryls, alkylaryls and arylalkyls;

$R_4$ and $R_6$ are independently selected from the group consisting of:
  (a) H, alkyl, aryl, arylalkyl, alkylaryl, substituted derivatives thereof, and $R_i$;
  (b) —C(O)OH and derivatives thereof, said derivatives selected from the group consisting of —C(O)OQ, —C(O)NR$_Y$R$_Z$, —C(O)[NHCHR$_{i(q)}$C(O)]$_q$OQ, and —C(O)[NHCHR$_{i(q)}$C(O)]$_q$NR$_Y$R$_Z$; and
  (c) —CHR$_i$NH$_2$ and derivatives thereof, said derivatives selected from the group consisting of —CHR$_i$NHW, —CHR$_i$NHC(O)OQ, —CHR$_i$NHC(O)R, —CHR$_i$NHC(O)NR$_Y$R$_Z$, —CHR$_i$NHC(O)[NHCHR$_{i(q)}$C(O)]$_q$OQ, —CHR$_i$NHSO$_2$R, and —CHR$_i$NH[C(O)CHR$_{i(r)}$NH]$_r$W,
    where q and r independently are integers from 1 to 10 inclusive;
    where J is a carboxyl protecting group;
    where G is an amino protecting group;
    where Q is H, R or J;
    where W is H, R or G;
  where each $R_i$ is independently selected from naturally or non-naturally occurring amino acid side chains;
    where R is alkyl, aryl, substituted aryl, alkylaryl, arylalkyl, or heterocyclic radical; and
    where each $R_Y$ and $R_Z$ is independently H, alkyl, aryl, substituted aryl, alkylaryl, arylalkyl, or heterocyclic radical.

In another aspect of the invention, a compound of the general formula III, is provided, and pharmaceutically acceptable salts thereof,

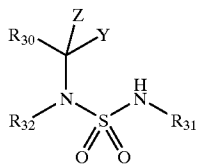

III wherein
- Z is a chemical species or $R_i$ capable of binding at a primary specificity site of a protease;
- Y is a chemical species reactive to a specific class of protease;
- $R_{30}$ is selected from the group consisting of hydrogen, alkyls, aryls, substituted aryls, alkylaryls or arylalkyls;
- $R_{31}$ is selected from the group consisting of alkyl, aryl, arylalkyl, alkylaryl, substituted derivatives thereof, $R_i$, —C(O)OQ, —C(O)NR$_Y$R$_Z$, —C(O)R, —SO$_2$R —[C(O)CHR$_{i(r)}$NH]$_r$W, —C(O)[NHCHR$_{i(q)}$C(O)]$_q$OQ, and —C(O)[NHCHR$_{i(q)}$C(O)]$_q$NR$_Y$R$_Z$; and
- $R_{32}$ is selected from the group consisting of alkyl, aryl, substituted aryl, arylalkyl, alkylaryl, $R_i$; —CHR$_i$C(O)O, —C(O)OQ, —C(O)NR$_Y$R$_Z$, —C(O)[NHCHR$_{i(q)}$C(O)]$_q$OQ, and —[C(O)CHR$_{i(r)}$NH]$_r$W;
  - where q and r independently are integers from 1 to 10 inclusive,
  - where Q is H, R or J, and J is a carboxyl protecting group,
  - where W is H, R or GI and G is an amino protecting group;
  - where each $R_i$ is independently selected from naturally or non-naturally occurring amino acid side chains,
  - where R is alkyl, aryl, substituted aryl, alkylaryl, arylalkyl, or heterocyclic radical, and
  - where each $R_Y$ and $R_Z$ is independently H, alkyl, aryl, substituted aryl, alkylaryl, arylalkyl, or heterocyclic radical.

In another aspect of the invention, a compound of the general formula IV is provided, and pharmaceutically acceptable salts thereof,

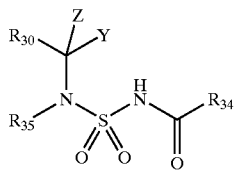

IV wherein
- Z is a chemical species or $R_i$ capable of binding at a primary specificity site of a protease;
- Y is a chemical species reactive to a specific class of protease;
- $R_{30}$ is selected from the group consisting of hydrogen, alkyls, aryls, alkylaryls or arylalkyls;
- $R_{34}$ is aryloxy, arylalkyl, —CHR$_i$NHW or —NHCHR$_i$C(O)OQ; and
- $R_{35}$ is alkyl, aryl, alkylaryl, arylalkyl or amino acid side group, $R_i$,
  - where Q is H, R or a carboxyl protecting group;
  - where W is H, R or an amino protecting group; and
  - where R is H, alkyl, aryl, substituted aryl, alkaryl, aralkyl, or heterocyclic radical.

In another aspect of the invention, a compound of the general formula V is provided and pharmaceutically acceptable salts thereof,

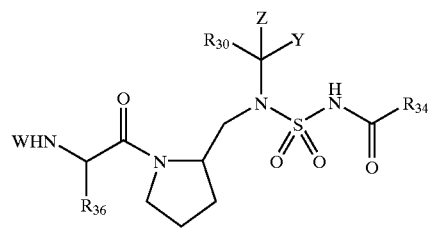

V wherein
- Z is a chemical species or $R_i$ capable of binding at a primary specificity site of a protease;
- Y is a chemical species reactive to a specific class of protease;
- $R_{30}$ is selected from the group consisting of hydrogen, alkyls, aryls, alkylaryls or arylalkyls;
- $R_{36}$ is alkyl, aryl, alkylaryl, arylalkyl or amino acid side group, $R_i$;
- $R_{34}$ is aryloxy, arylalkyl, —CHR$_i$NHW or —NHCHR$_i$C(O)OQ,
  - where Q is H, R or a carboxyl protecting group;
  - where W is H, R or an amino protecting group; and
  - where R is H, alkyl, aryl, substituted aryl, alkaryl, aralkyl, or heterocyclic radical.

In still another aspect of the invention, a compound having the general formula II, and pharmaceutically acceptable salts thereof, is provided,

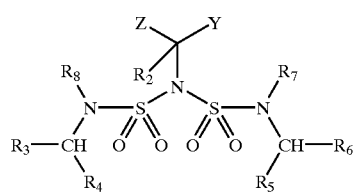

II wherein
- Z is a chemical species or $R_i$ capable of binding at a primary specificity site of a protease inhibitor;
- Y is a chemical species reactive to a specific class of protease inhibitor;
- each of $R_2$, $R_3$, $R_5$, $R_7$ and $R_8$ is independently selected from the group consisting of hydrogen, and saturated, unsaturated and aromatic hydrocarbons, and more particularly, hydrogen, alkyls, aryls, alkylaryls or arylalkyls; and
- $R_4$ and $R_6$ are independently selected from the group consisting of:
  - (a) H, alkyl, aryl, arylalkyl, alkylaryl, substituted derivatives thereof, and $R_i$;
  - (b) —C(O)OH and derivatives thereof, said derivatives selected from the group consisting of —C(O)OQ, —C(O)NR$_Y$R$_Z$, —C(O)[NHCHR$_{i(q)}$C(O)]$_q$OQ, and —C(O)[NHCHR$_{i(q)}$C(O)]$_q$NR$_Y$R$_Z$; and
  - (c) —CHR$_i$NH$_2$ and derivatives thereof, said derivatives selected from the group consisting of —CHR$_i$NHW, —CHR$_i$NHC(O)OQ, —CHR$_i$NHC(O)R, —CHR$_i$NHC(O)NR$_Y$R$_Z$, —CHR$_i$NHC(O)[NHCHR$_{i(q)}$C(O)]$_q$OQ, —CHR$_i$NHSO$_2$R, and —CHR$_i$NH[C(O)CHR$_{i(r)}$NH]$_r$W, where q and r independently are integers from 1 to 10 inclusive;
where J is a carboxyl protecting group;
where G is an amino protecting group;
where Q is H, R or J;
where W is H, R or G;
where each $R_i$ is independently selected from naturally or non-naturally occurring amino acid side chains;
where R is alkyl, aryl, substituted aryl, alkylaryl, arylalkyl, or heterocyclic radical; and
where each $R_Y$ and $R_Z$ is independently H, alkyl, aryl, substituted aryl, alkylaryl, arylalkyl, or heterocyclic radical.

In yet another aspect of the invention, a compound of the general formula VI, and pharmaceutically acceptable salts thereof, is provided,

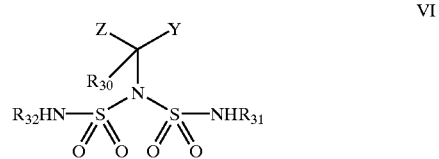

VI wherein
Z is a chemical species or $R_i$ capable of binding at a primary specificity site of a protease;
Y is a chemical species reactive to a specific class of protease;
$R_{30}$ is selected from the group consisting of hydrogen, alkyls, aryls, alkylaryls or arylalkyls;
$R_{31}$ is selected from the group consisting of alkyl, aryl, arylalkyl, alkylaryl, substituted derivatives thereof, $R_i$, —C(O)OQ, —C(O)NR$_Y$R$_Z$, —C(O)R, —SO$_2$R —[C(O)CHR$_{i(r)}$NH]$_r$W, —C(O)[NHCHR$_{i(q)}$C(O)]$_q$OQ, and —C(O)[NHCHR$_{i(q)}$C(O)]$_q$NR$_Y$R$_Z$; and
$R_{32}$ is selected from the group consisting of alkyl, aryl, substituted aryl, arylalkyl, alkylaryl, $R_i$; —CHR$_i$C(O)O, —C(O)OQ, —C(O)NR$_Y$R$_Z$, —C(O)[NHCHR$_{i(q)}$C(O)]$_q$OQ, and —[C(O)CHR$_{i(r)}$NH]$_r$W;
where q and r independently are integers from 1 to 10 inclusive,
where Q is H, R or J, and J is a carboxyl protecting group,
where W is H, R or G, and G is an amino protecting group;
where each $R_i$ is independently selected from naturally or non-naturally occurring amino acid side chains,
where R is alkyl, aryl, substituted aryl, alkylaryl, arylalkyl, or heterocyclic radical, and
where each $R_Y$ and $R_Z$ is independently H, alkyl, aryl, substituted aryl, alkylaryl, arylalkyl, or heterocyclic radical.

The invention features a universal template for creating biologically active, peptidomimetic compounds, such as those of formulae I–VI, above. The chemical stability, side chain orientation, and polarity characteristics of the disclosed core template combine to provide numerous inhibitors of a variety of enzymes, including serine and cysteine proteases and matrix metalloproteases (MMPs) and aspartic proteases and others. The disclosed compounds are designed to have inhibitory activity, including selectivity and improved subsite interactions, by varying the pendant groups of the template compounds.

The disclosed inhibitors are useful in methods of treating a protease-related condition, such as a degenerative disease, wherein a pharmaceutically effective amount of a composition including one or more disclosed inhibitors is administered to a patient. The invention therefore further includes methods of reducing or inhibiting protease activity by contacting a protease with one of the compounds I–VI above. The protease may be from any protease source, including human and non-human mammals, and tissues, cells or membranes isolated therefrom which include the protease, or an isolated enzyme which has a binding affinity for the compounds of the invention. Binding affinity is defined as having a $K_i$ on the order of at least micromolar ($\mu$M) and preferably nanomolar (nM).

Other features and advantages of the invention will be apparent from the detailed description and examples below.

DETAILED DESCRIPTION OF THE INVENTION

Figure 1:
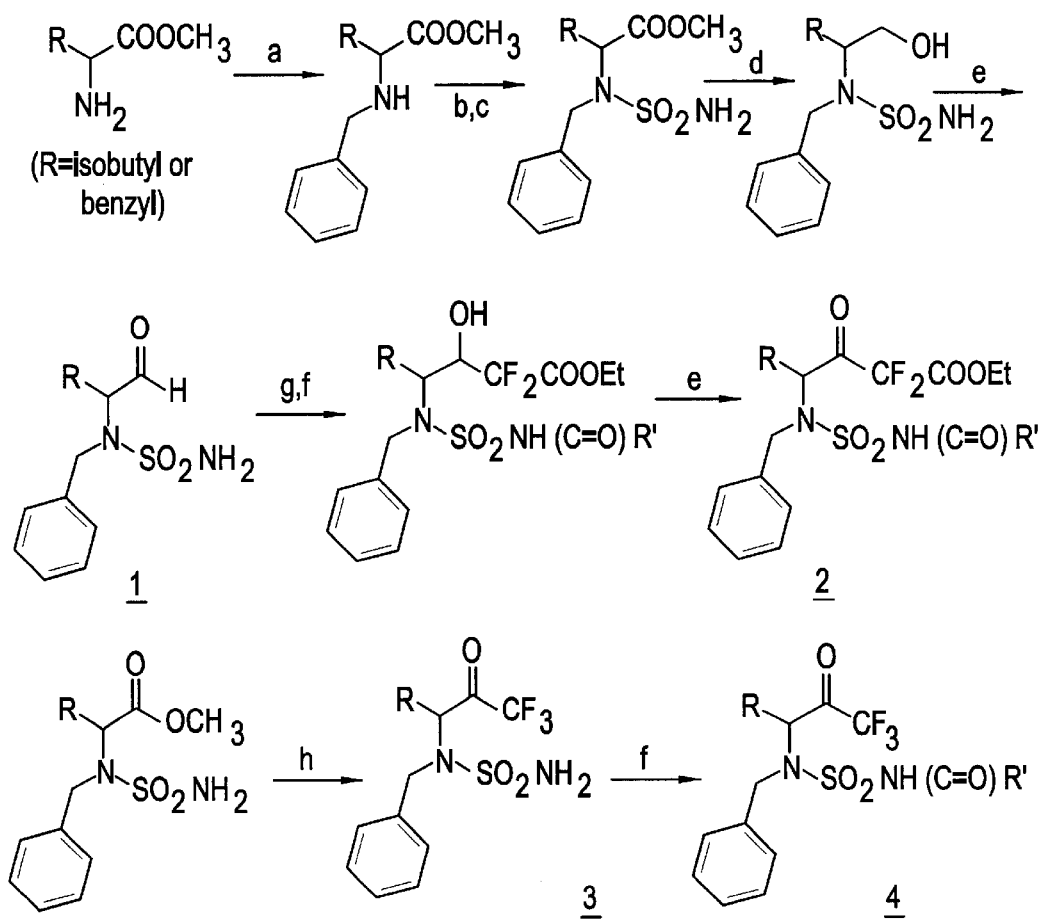
FIG. 1 shows a general reaction scheme for the preparation of serine protease inhibitors. Script below the drawing refers to reagents used to obtain the desired chemical reaction or purification step.

Proteolysis is a highly specific process, involving both the sequential and conformational recognition of the enzyme substrate. By sequential recognition, it is meant the presence of multiple recognition elements on the protease inhibitor which mimic the order of presentation of such sites on the protease enzyme itself. By conformational recognition, it is meant the three dimensional structure of the receptor site on the protease. An example of an integrated sequential and conformational design is the formation of sequential recognition elements spatially organized along a structural backbone which mimics the conformational geometry of the substrate. The present invention provides a backbone structure that integrates both sequential and conformational design features.

Enzyme selectivity can be optimized by the appropriate selection of Z to serve as the primary specificity group, $P_1$, which is accommodated in the $S_1$ subsite of the target enzyme. The term "primary specificity group" is used herein to mean the pendant chemical group that preferentially interacts and/or is accommodated by the corresponding subsite on the targeted proteolytic enzyme. $S_1, S_2, \ldots S_n$ and $S'_1, S'_2 \ldots S'_n$ correspond to the enzyme subsites on either side of the reactive bond in the enzyme. In sequentially designed protease inhibitors, each subsite ideally corresponds to amino acid side chains or analogues thereof, designated $P_1, P_2 \ldots P_n$ and $P'_1, P'_2 \ldots P'_n$, respectively, of the inhibitor molecule.

In another aspect of the invention, bis-amide compounds, such as compounds II and VI, include a bis-sulfamide structural backbone of the formula, $-N-SO_2-N-SO_2-N-$, which provides additional separation between the secondary specificity sites on the molecule. The bis-sulfamide structural backbone provides restricted conformational mobility which is entropically favored. The spatial arrangement of the core structure is expected to present the Z group for binding to the active site, while allowing for a geometry of the pendant $R_4$ and $R_6$ groups that closely follows or complements that of the secondary sites, e.g., $S_1$, $S_2 \ldots S_n$ and $S'_1, S'_2 \ldots S'_n$.

Descriptions and discussions relating to the selection and structure and activity of substituents may apply equally to either compound except as specifically noted, and to all other compounds described herein as being part of the invention.

In compounds I–VI, Z is the primary specificity group (fits into the primary specificity pocket $S_1$ of a target protease). It is the primary determinant of enzyme selectivity. For example, serine protease trypsin prefers a basic side chain (i.e. Lys or Arg side chains) for Z, while HLE prefers a medium size hydrophobic group such as isopropyl or isobutyl (i.e., Val or Leu side chains). Preferably, a benzyl group, i.e., a Phe side chain, is introduced for Z in order to enhance inhibition of Cath G or chymotrypsin. Hence, depending on which enzyme one would like to inhibit and based on the known preference of a protease for a primary specificity site, a selection is made of an amino acid that has the correct side chain. Table 1 lists a variety of proteolytic enzymes and the nature of the Z-group residue which effectively inhibits that enzyme.

TABLE 1

| Protease | Type of protease | Z-group inhibitor type[a] | amino acid side group ($R_i$) for Z |
|---|---|---|---|
| proteinase 3 (PR-3) | serine | H | n-propyl, ethyl |
| HLE | serine | H | isopropyl, isobutyl |

TABLE 1-continued

| Protease | Type of protease | Z-group inhibitor type[a] | amino acid side group ($R_i$) for Z |
|---|---|---|---|
| chymase | serine | H | benzyl |
| HCV protease | serine | H | methyl or n-propyl |
| cathepsin G | serine | H | benzyl |
| cytomegalovirus | serine | H | methyl |
| tyrptase | serine | B | $-(CH_2)_4NH_2$; $-(CH_2)_3NH(C=NH)NH_2$ |
| granzyme B | serine | A | $-CH_2COOH$ |
| cathepsin K | cysteine | H/B | isobutyl, $-(CH_2)_4NH_2$; $-(CH_2)_3NH(C=NH)NH_2$ |
| calpains | cysteine | H | isobutyl |
| gingipains | cysteine | B | $-(CH_2)_4NH_2$; $-(CH_2)_3NH(C=NH)NH_2$ |
| HR 3C | cysteine | B | $CH_2CH_2CONH_2$ |
| caspases | cysteine | A | $CH_2COOH$ |
| metalloproteases | MMP | H | isopropyl, isobutyl, benzyl |

[a]H = hydrophobic/neutral; B = basic; A = acidic

The nature of Z is important for inhibitor recognition, i.e., it makes possible the binding of the inhibitor to the active site of an enzyme. After the inhibitor binds it forms an enzyme:inhibitor complex. The strength of binding is determined by Z and additional interactions with secondary specificity sites. The nature of Y determines which class of protease will react with the inhibitor. Therefore, Y determines which class of protease will be inhibited, while Z primarily determines which protease within a given class will be inhibited.

Although compounds of the invention are linear molecules, the sulfamide moiety serves as a rigid pivot that orients the $Z/R_2$, $R_3/R_4$, and $R_5/R_6/R_7$ towards the appropriate subsites on the target enzyme, $S_1$, $S_2-S_n$ and $S'_2-S'_n$, respectively. The moiety, $N-SO_2-N$, serves as a rigid pivot due to extended electron-pair interactions among the neighboring heteroatoms. Thus, potency, as well as enzyme selectivity, may be optimized by using appropriate substituent selections.

When identifying a compound having serine protease inhibitory properties, Y is preferably a moiety capable of reacting with the hydroxyl group of the active site serine. In preferred embodiments, Y is a carbonyl-containing compound and preferably includes aldehydes, ketones, α-ketocarbonyls, and alkylhaloketocarbonyls. In particular, Y may be selected from the group consisting of $-CHO$, $-C(O)R_{21}$, $-C(O)C(O)R_{22}$, and $-C(O)CF_2C(O)R_{22}$, where $R_{21}$ is an activated heterocyclic, $C_{1-2}$ haloalkyl, amino, C(O)O-PEG or C(O)NH-PEG, where $R_{22}$ is $OR_{23}$, $NR_yR_z$, or $-[NHCHR_{i(n)}C(O)]_nOR_{25}$, where n is an integer in the range of 1 to 10, where PEG=polyethylene glycol, and where $R_{23}$ is alkyl, arylalkyl, aryl, or substituted aryl. Suitable activated heterocyclics are those which serve to withdraw electrons making the carbonyl carbon to which it is attached more electrolphilic and consequently more susceptible to nucleophilic attack. Exemplary heterocyclics include:

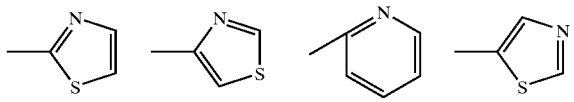

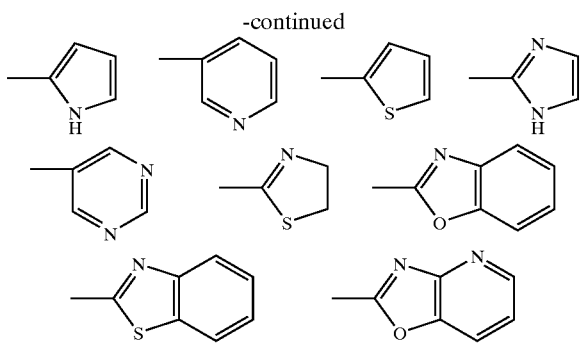

Particularly preferred activated heterocyclics include:

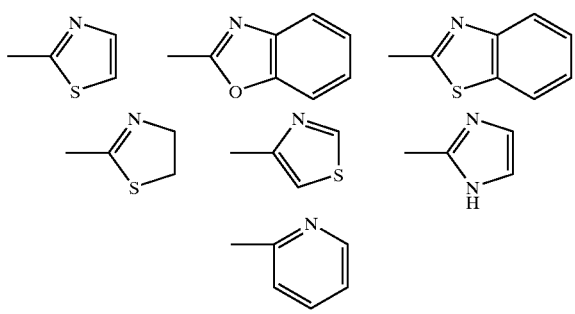

When identifying a compound having cysteine protease inhibitory properties, Y is preferably a moiety capable of reacting with the basic sulfhydryl group of the active site cysteine. In preferred embodiments, Y may be an aldehyde, substituted-alkylketone, epoxide or a Michael acceptor ($\alpha,\beta$-unsaturated group). In preferred embodiments, for a cysteine protease inhibitor, Y includes —CHO, —CH=CHX, epoxide and —C(O)CH$_2$V, where X is a group capable of electron delocalization, and V is a leaving group. Exemplary X groups include carboxylic acids and esters, nitriles and alkylthionyls, such as —SO$_2$R$_{26}$. Exemplary V groups include halide, —OC(O)R$_{26}$, phenoxide, substituted phenoxide, —N(SO$_2$R$_{26}$)C(O)R$_{27}$, —N(SO$_2$R$_{26}$)[C(O)NHCHR$_i$C(O)]$_m$OR, where m=1,2, and

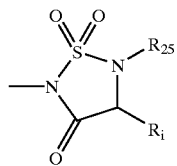

where
R$_{25}$ is alkyl or hydrogen, R$_{26}$ is alkyl, aryl, substituted aryl, or arylalkyl, and
R$_{27}$ is alkyl, aryl, substituted aryl, arylalkyl, or CHR$_i$NHW.

When identifying a compound having metalloprotease inhibitory properties, Y is preferably a moiety capable of binding with zinc. Suitable Y includes groups such as —CH$_2$SR$_{24}$, —COOH, or —C(O)NHOR$_{29}$, and —CH$_2$PO(OH)$_2$, where R$_{24}$ is H, acylalkyl or acylaryl and R$_{29}$ is H, alkyl or arylalkyl.

In preferred embodiments, R$_2$ is H, thereby making the carbon to which Y, Z and R$_2$ are attached chiral and having the L configuration; however, in other preferred embodiments, R$_2$ can also be an alkyl or arylalkyl group.

In other preferred embodiments, the compounds are peptidomimetic. Peptidomimetic is used herein in a broad sense to designate organic molecules mimicking some properties of peptide ligands. The peptidomimetic compound includes substituents that are selected from the group of amino acid side groups, amino acids or modified derivatives thereof, which mimic the structure and function of peptides.

Thus, in preferred embodiments, R$_4$ and R$_6$, or R$_{31}$ and R$_{32}$, may represent groups which are side chain moieties from naturally and non-naturally occurring amino acids. Selection of suitable R$_4$ and R$_6$, or R$_{31}$ and R$_{32}$, may provide secondary or tertiary structures which mimic the secondary subsites of the targeted proteolytic enzyme.

In preferred embodiments, R$_4$ and R$_6$, or R$_{31}$ and R$_{32}$, independently may be a carboxylic acid moiety, e.g., —COOH, or derivatives thereof which present an "amino acid-like" structure. Exemplary derivatives include esters, protected carboxyl groups, amides, and condensates with amino acids and ester and amido derivatives thereof.

In other preferred embodiments, R$_4$ and R$_6$ or R$_{31}$ and R$_{32}$, independently may be an alkyl amine moiety, e.g., —CHR$_i$NH$_2$ or derivatives thereof which present an "amino acid-like" structure. Exemplary derivatives include protected amines, sulfonamides, amides, and the like, and condensates with amino acids and protected, ester and amido derivatives thereof.

Another example is a molecule of formula I or formula II, wherein R$_4$ is CHR$_i$NH$_2$ and R$_6$ is COOH, i.e., a non-natural amino acid which can be incorporated into a peptide or peptidomimetic (or libraries thereof) by combinatorial or standard synthetic methodology. Other compositions of formula I are suitable, such as those wherein: R$_4$ is amino and R$_6$ is carboxyl; R$_4$ is carboxyl or protected carboxyl and R$_6$ is amino or protected amino; R$_4$ is carboxyl or protected carboxyl, and R$_6$ is —CH(R$_i$)NHW where W is H or G; each of R$_4$ and R$_6$ is carboxyl or protected carboxyl; each of R$_4$ and R$_6$ is amino or protected amino; and each of R$_4$ and R$_6$ is —CH(R$_i$)NHW.

In preferred embodiments, pendant groups such as R$_4$ and P$_6$, or R$_{31}$ and R$_{32}$, are amino- or carboxyl-terminated, in a manner analogous to a natural or non-natural amino acid to provide a peptidomimetic compound. The invention features some compounds which have two or more amino acid residues linked by amide bonds, e.g., [NHCHR$_{i(q)}$CO]$_q$ or [C(O)CHR$_{i(r)}$NH]$_r$, and the like, where each R$_i$ is an amino acid side chain. Where q (or r and the like) is between 1 and 10, the moiety can have between 1 and 10 amino acid residues (monomer to decamer). Each amino acid side chain is selected independently, and there may be two separate amino acid sequences, one represented by moiety R$_4$ (or R$_{32}$) and the other by moiety R$_6$ (or R$_{31}$). For example, if q=3 for R$_4$, then R$_4$ is —C(O)[NHCHR$_1$C(O)]—[NHCHR$_2$C(O)]—[NHCHR$_3$C(O)]—X, and if r=4 for R$_6$, then R$_6$ is —CHR$_i$NH[C(O)CHR$_1$NH]—[C(O)CHR$_2$NH]—[C(O)CHR$_3$NH]—[C(O)CHR$_4$NH]—X, where X is a suitable end group as described herein, and where each amino acid is independently selected. In many of the known proteases, 3–4 subsites have been identified on either side of the primary specificity site. In preferred embodiments, r and q are in the range of 2–5, inclusive, and are selected to have affinity for known or suspected enzyme subsites on either side of the active site.

In other preferred embodiments, R$_4$ and R$_6$, or R$_{31}$ and R$_{32}$, contain amino acid or amino-acid-type groups and the C-terminal to N-terminal orientation is discontinuous. In other words, the molecule may be, from left to right, N-terminal to C-terminal until the inhibitor monomer is reached ($R_4$) then (continuing to the right from $R_6$) the molecule is C-terminal to N-terminal. This separation and reverse C-/N-terminal orientation can allow inhibition of two or more enzymes oriented diagonally across the molecule using an oligomer of overall smaller molecular weight, since the discontinuity provides more space between the enzymes, relative to a repeated sequence along the same length and side. The reverse C-/N-terminal orientation, and the length of the peptide or peptidomimetic sequences attached to $R_4$ and $R_6$ can also bring two or more enzymes or receptors in proximity to each other in a desired conformation to promote further interaction. The sequences attached to $R_4$ and $R_6$ may interact with each other to form a secondary or tertiary structure that enhances the activity of one or more inhibitor monomers, e.g., by mimicking subsites or other local protein structure environments. Disclosed compounds can also be used to inhibit protein folding, e.g., aggregation of tetrameric or dimeric proteins or protein-protein interactions.

In another aspect of the invention, the compound has the formula III.

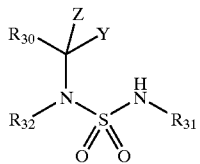

III

In formula III, Y and Z are selected as described above and $R_{30}$ is selected from the group consisting of hydrogen, and saturated, unsaturated and aromatic hydrocarbons, and more particularly, hydrogen, alkyls, aryls, alkylaryls or arylalkyls, and most preferably is hydrogen.

$R_{31}$ is selected from the group consisting of alkyl, aryl, arylalkyl, alkylaryl, substituted derivatives thereof, $R_i$, —C(O)OQ, —C(O)NR$_Y$R$_Z$, —C(O)R, —SO$_2$R —[C(O)CHR$_{i(r)}$NH]$_r$W, —C(O)[NHCHR$_{i(q)}$C(O)]$_q$OQ, and —C(O)[NHCHR$_{i(q)}$C(O)]$_q$NR$_Y$R$_Z$; and $R_{32}$ is selected from the group consisting of alkyl, aryl, substituted aryl, arylalkyl, alkylaryl, $R_i$; —CHR$_i$C(O)O, —C(O)OQ, —C(O)NR$_Y$R$_Z$, —C(O)[NHCHR$_{i(q)}$C(O)]$_q$OQ, and —[C(O)CHR$_{i(r)}$NH]$_r$W; where q and r independently are integers from 1 to 10 inclusive, Q is H, R or J, and J is a carboxyl protecting group, W is H, R or G, and G is an amino protecting group; each $R_i$ is independently selected from naturally or non-naturally occurring amino acid side chains, R is alkyl, aryl, substituted aryl, alkylaryl, arylalkyl, or heterocyclic radical, and each $R_Y$ and $R_Z$ is independently H, alkyl, aryl, substituted aryl, alkylaryl, arylalkyl, or heterocyclic radical.

In another aspect of the invention, the compound has the formula IV.

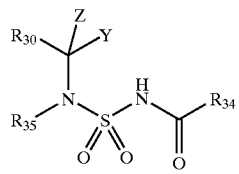

IV

In formula IV, Y, Z and $R_{30}$ are selected as described above. $R_{34}$ is aryloxy, arylalkyl, —CHR$_i$NHW or —NHCHR$_i$C(O)OQ, where W and Q are as defined above, and $R_{35}$ is alkyl, aryl, alkylary, arylalkyl or amino acid side group, $R_i$, and CHR$_i$C(O)OH and derivatives thereof. Exemplary derivatives include —C(O)OQ, —C(O)NR$_Y$R$_Z$, —C(O)[NHCHR$_{i(q)}$C(O)]$_q$OQ, where Q is H, R or J, and J is a carboxyl protecting group.

In preferred embodiments, $R_{35}$ is selected to be an amino acid side group, $R_i$, in particular one which has affinity for secondary binding sites on the protease of interest. In the case of serine or cysteine protease inhibitors, $R_{35}$ is preferably methyl or benzyl. In the case of metalloprotease inhibitors, $R_{35}$ is preferably isopropyl, isobutyl or benzyl.

In preferred embodiments, $R_{34}$ includes a benzyl group, that is $R_{34}$ is benzyloxy, benzyl, ethylphenyl, or an amino acid derivative in which $R_i$ includes a benzyl group, i.e., phenylalanine. This is because many proteases, in particular serine proteases, and specifically, elastase, prefer a benzyl group at the S'$_2$ position.

In preferred embodiments, W is H, Boc or Cbz and Q is H or methyl.

In another aspect of the invention, a compound of the formula V is provided.

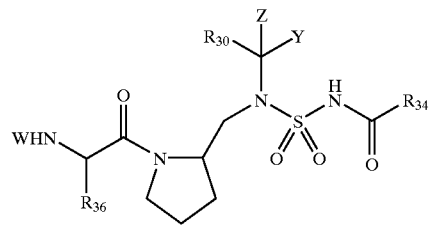

V

In formula V, Y, Z and $R_{30}$ are selected as described above. $R_{36}$ is alkyl, aryl, alkylary, arylalkyl or amino acid side group, $R_i$, and $R_{34}$ is aryloxy, arylalkyl, CHR$_i$NHW or —NHCHR$_i$C(O)OQ, where $R_i$, W and Q are as defined above.

In preferred embodiments, $R_{34}$ includes a benzyl group, that is $R_{34}$ is benzyloxy, benzyl, ethylphenyl, or an amino acid derivative in which $R_i$ includes a benzyl group, i.e., phenylalanine. This is because many proteases, in particular serine proteases, and specifically, elastase, prefer a benzyl group at the S'$_2$ position.

In preferred embodiments, $R_{36}$ is selected to be an amino acid side group, $R_i$, in particular one which has affinity for secondary binding sites on the protease of interest. Compound V differs most significantly from compound IV by introduction of a proline residue at the nitrogen bearing the "CR$_{30}$YZ" moiety. The proline residue fits into the S$_2$ subsite of many proteases, in particular, elastase, PR3, Cat G. The compound is also capable of accommodating an additional residue at the $R_{36}$ position to bind in the S$_3$ position of the protease and/or provide additional contacts, e.g., hydrogen binding, hydrophobic interactions, etc., with the enzyme to enhance binding. In the case of serine proteases, e.g., elastase, Cat G, $R_{36}$ is preferably methyl or isopropyl.

In preferred embodiments, W is H, Boc or Cbz and Q is H or methyl.

In another aspect of the invention, a compound of the formula VI and pharmaceutically acceptable salts thereof is provided.

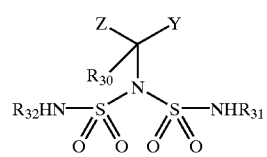

VI

In preferred embodiments of compound VI, Z, Y and $R_{30}$ are as defined herein above. $R_{31}$ is selected from the group consisting of alkyl, aryl, arylalkyl, alkylaryl, substituted derivatives thereof, $R_i$, —C(O)OQ, —C(O)$NR_YR_Z$, —C(O)R —SO$_2$R —[C(O)$CHR_{i(r)}$NH]$_r$W, —C(O)[NHCHR$_{i(q)}$C(O)]$_q$OQ, and —C(O)[NHCHR$_{i(q)}$C(O)]$_q$NR$_Y$R$_Z$; and $R_{32}$ is selected from the group consisting of alkyl, aryl, substituted aryl, arylalkyl, alkylaryl, $R_i$; —CHR$_i$C(O)O, —C(O)OQ, —C(O)NR$_Y$R$_Z$, —C(O)[NCHR$_{i(q)}$C(O)]$_q$OQ, and —[C(O)CHR$_{i(r)}$NH]$_r$W; where q and r independently are integers from 1 to 10 inclusive, Q is H, R or J, and J is a carboxyl protecting group, W is H, R or G, and G is an amino protecting group; each $R_i$ is independently selected from naturally or non-naturally occurring amino acid side chains, R is alkyl, aryl, substituted aryl, alkylaryl, arylalkyl, or heterocyclic radical, and each $R_Y$ and $R_Z$ is independently H, alkyl, aryl, substituted aryl, alkylaryl, arylalkyl, or heterocyclic radical.

In preferred embodiments, $R_{32}$ is selected to be an amino acid side group, $R_i$, in particular one which has affinity for secondary binding sites on the protease of interest. In the case of serine or cysteine protease inhibitors, $R_{32}$ is preferably methyl or benzyl. In the case of metalloprotease inhibitors, $R_{32}$ is preferably isopropyl, isobutyl or benzyl.

Table 2 lists a variety of proteases and identifies the preferred compound IV and V targeted for its inhibition.

TABLE 2

| protease | Z | Y | $R_{35}$ (IV) or $R_{36}$ (V) | $R_{34}$ |
|---|---|---|---|---|
| | | Serine Proteases | | |
| elastase | isopropyl; isobutyl | C(O)CF$_3$, C(O)CF$_2$C(O)OEt; C(O)2-benzoxazole; C(O)2-thiazole; C(O)oxadiazole | methyl; benzyl | OCH$_2$Ph; CH$_2$CH$_2$Ph; CH(CH$_2$Ph)NHW; CH(CH$_2$Ph)COOQ |
| proteinase 3 | n-propyl; ethyl | as for elastase | as for elastase | as for elastase |
| cathepsin G | benzyl | as for elastase | as for elastase | as for elastase |
| chymase | benzyl | as for elastase | as for elastase | as for elastase |
| tryptase | (CH$_2$)$_4$NH$_2$; (CH$_2$)$_3$(C=NH)NH$_2$ | as for elastase | as for elastase | as for elastase |
| granzyme B | CH$_2$COOH | as for elastase | as for elastase | as for elastase |
| HCV protease | methyl; n-propyl | as for elastase | as for elastase | as for elastase |
| cytomegalovirus protease | methyl | as for elastase | as for elastase | as for elastase |
| | | Cysteine Proteases | | |
| cathepsin K | isobutyl; (CH$_2$)$_4$NH$_2$; (CH$_2$)$_3$(C=NH)NH$_2$ | CH=CH(CO)OEt; CH=CHSO$_2$CH$_3$/Ph; (CO)CH$_2$O(CO)Ph, (CO)CH$_2$F, CHO | as for elastase | as for elastase |
| gingipains | (CH$_2$)$_4$NH$_2$; (CH$_2$)$_3$(C=NH)NH$_2$ | as for cathepsin K | as for elastase | as for elastase |
| calpains | isobutyl | as for cathepsin K | as for elastase | as for elastase |
| caspases | CH$_2$COOH | as for cathepsin K | as for elastase | as for elastase |
| HR 3C | CH$_2$CH$_2$(CO)NH$_2$ | as for cathepsin K | as for elastase | as for elastase |
| | | Metalloproteases | | |
| metalloproteases | isopropyl; isobutyl; benzyl | C(O)NHOH | as for elastase | as for elastase |

Inhibitor compounds of the types I–VI can be formed using synthetic organic chemistry, combinatorial or matrix techniques or as described herein below and subsequently assayed for biological activity, including inhibition of enzymes. It is preferred that the compounds demonstrate inhibition ($K_i$) of the target enzyme in the nanomolar (nM) range. In practical terms this means that less compound is required for inhibition, thereby minimizing toxic or side effects. $K_i$ may be minimized by increasing the binding strength of the compound to the target enzyme. This is accomplished in the compounds of the invention by increasing the number of sites in the inhibitor compound available for favorable interaction with the target protease. By way of example, the compounds of formula V which provide three subsite specific binding moieties may be expected to bind more strongly (and hence have a lower $K_i$) than compounds of formula III or IV. Peptidomimetic compounds of formula I, II, or III having multiple sites for enzyme binding may demonstrate even stronger enzyme:inhibitor binding.

Screening of compounds for protease activity is known in the art. The human leukocyte elastase (HLE), cathepsin G (Cat G) and proteinase 3 (PR3) assays have each been described in detail; see, Groutas et al. *Biochemistry* 36:4739 (1997). Chymase assay has also been previously reported; see, Schechter, et al., *J. Biol. Chem.* 268:23626 (1993).

Thermolysin activity with or without inhibitor was measured using N-[3-[2-Furyl]acryloyl]-Gly-L-Leu-NH$_2$ as substrate (Walsh, K. A. et al. *Methods Enzymol.*34:435 (1974; Nishino, N. et al. *Biochemistry* 17:2846 (1978). The substrate solution in 0.1 M Tris-HCl buffer (pH 7.2) containing 2% DMF was added to thermolysin in 0.1 M Tris-HCl, ph 7.2, containing 10 mM CaCl$_2$ and the decrease in absorbance at 345 nm was monitored using a Hewlett-Packard diode array UV/VIS spectrophotometer at 25° C. Percent inhibition and/or $K_1$ values were determined from Dixon plots (Dixon, M. *Biochem, J.* 55:70 (1953) at two different substrate concentrations.

The substrates and buffers used in the assay inhibition studies with human leukocyte elastase (HLE), cathepsin G (Cat G), proteinase 3 (PR3) (Groutas, W. C., et al., *Biochemistry* 36:4739 (1997) and chymase (Groutas, W. C. et al., *Bioorg. Med. Chem. Lett.* 9:2199 (1999) were as follows: HLE, MeOSuc-AAPV-pNA, 0.1 M HEPES buffer, pH, 7.25 in 1–5% DMSO; Cat G, Suc-AAPF-pNA, 0.1 M HEPES buffer, pH 7.5; PR3, Boc-L-Ala p-mitrophenyl ester, 0.1 M phosphate buffer, pH 6.5; chymase, Suc-AAPF-pNA, 0.45 Tris buffer, 1.8 M Na Cl, pH 8.03 and 2% DMSO. All assays were carried out at 25° C. and for all enzymes the absorbance was monitored at 410 nm, except PR 3 (348 nm).

Substrates and buffers used in the enzymes assays for other enzymes were the following: for trypsin, benzoyl-L-Arg p-nitroanilide, 0.025 M phosphate buffer, pH 7.51 in 2% DMSO; tryptase, Tosyl-Gly-Pro-Lys-pNA, 0.1M HEPES buffer, pH 8.0, 0.2 M NaCl, 10 uM heparin; granzyme B, Boc-Ala-Ala-Pro-Asp-pNA in 20 mM HEPES buffer, 0.1 M NaCl, pH 7.4.

Some terms are defined below and elsewhere in the disclosure.

Alkyls may be substituted or unsubstituted and may be linear, branched, or cyclic. Preferably, alkyl groups are between 1 and 10 carbon atoms, and more preferably between 1 and 6 carbon atoms. Examples of alkyls include methyl, ethyl, propyl, isopropyl, butyl, isobutyl, sec-butyl, t-butyl, pentyl, cyclopentyl, isopentyl, neopentyl, t-pentyl, sec-pentyl, hexyl, cyclohexyl, isohexyl, 2,3-dimethylbutyl, 2,2-dimethylbutyl, 3-ethylpentyl, 3,4-dimethylpentyl, heptyl, octyl, nonyl, decyl, and (2,3,4-trimethylcyclohexyl) methyl. An alkylene is a bivalent hydrocarbon, e.g., an alkyl group with an additional hydrogen removed, such as methylene, propylene, or 1,4-cyclohexylene. Alkoxy groups are alkyl groups terminated by an oxygen. Alkoxy groups also include polyethers, such as methoxyethoxy.

Alkenyls are alkyl groups with one or more unsaturated carbon-carbon bonds, such as cyclopentenyl, cyclopentadienyl, cyclohexadiene, but-2-enyl, 3,4-dimethylpent-3-enyl, allyl, vinyl, prenyl, and isoprenyl. Alkenylenes include vinylene and propenylene.

Amino acid side chains include the side chains of natural and non-natural amino acids, which may be protected or unprotected, or otherwise modified. Natural amino acids include glycine, alanine, valine, leucine, isoleucine, serine, threonine, aspartic acid, asparagine, lysine, glutamic acid, glutamine, arginine, histidine, phenylalanine, cysteine, tryptophan, tyrosine, methionine, and proline. Others include lanthionine, cystathionine, and homoserine. Some unusual or modified amino acids include 2-aminoadipic acid, 3-aminoadipic acid, beta-alanine, 2-aminobutyric acid, 4-aminobutyric acid, 6-amino-caproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, 6-N-methyllysine, N-methylvaline, norvaline, norleucine, and ornithine. Non-natural amino acids include 1-aminosuberic acid, 3-benzothienylalanine, 4,4'-biphenylalanine, 4-bromophenylalanine, 2-chlorophenylalanine, 3-chlorophenylalanine, 4-chlorophenylalanine, 3-cyanophenylalanine, 4-cyanophenylalanine, 3,4-dichlorophenylalanine, 3,4-difluorophenylalanine, 3,5-difluorophenylalanine, 2-fluorophenylalanine, 3-fluorophenylalanine, 4-fluorophenylalanine, 3,3-diphenylalanine, homophenylalanine, 2-indanylglycine, 4-iodophenylalanine, 1-naphthylalanine, 2-naphthylalanine, 4-nitrophenylalanine, pentafluorophenylalanine, 2-pyridylalanine, 3-pyridylalanine, 4-pyridylalanine, tetrahydroisoquinoline-3-COOH, 4-thiazolalanine, 2-thienylalanine, 3-trifluoroethylphenylalanine, 4-trifluoromethylphenylalanine, 3,5-dibromotyrosine, 3,5-diiodotyrosine, hydroxylysine, thienylalanine, γ-carboxyglutamate, phosphotyrosine, phosphoserine, 3,4,5-trifluoromethyl-phenylalanine, as well as glycosylated amino acids, such as glycosylated serine, asparagine and threonine. The term "side chain" is well known in the art; for example, the side chains of leucine and phenylalanine are isobutyl (or 2-methylpropyl) and benzyl, respectively.

Protected amino acid side chains are side chains that have reactive functionalities such as hydroxyl (Ser, Thr), thiol (Cys), carboxylic acid (e.g., Asp, Glu, or any C-terminal amino acid), or amino (e.g., Asn, Gln, Lys, Arg, and any free N-terminal amino acid) which are masked by a protecting group. For example, a hydroxyl group can be protected as an ether or ester, a thiol group can be protected as a thioether or thioester, a carboxylic acid can be protected as an ester, amide, or hydrazide, and an amino group can be protected as a carbamate or amide. Methods of protecting and deprotecting (or deblocking) a functionality are well-known to those in the art and described in detail in, e.g., *Protective Groups in Organic Synthesis*, by T. W. Greene and P. G. M. Wuts, John Wiley & Sons, 3rd Ed. (1999).

Amino protecting groups ("G") include carbamates and amides. Carbamates include methyl, ethyl, 9-fluorenylmethyl, 9-(2-sulfo)fluorenylmethyl, 9-(2,7-dibromo)fluorenylmethyl, 2,7-di-t-butyl[9-(10,10-dioxo-10,10,10,10-tetrahydrothioxanthyl)]methyl, and 4-methoxyphenacyl. Others include 2,2,2-trichloroethyl, 2-trimethysilylethyl, 2-phenylethyl, t-butyl, vinyl, allyl, cinnamyl, benzyl, and substituted benzyls, 2-methylthioethyl. Amides include N-formyl, N-acetyl, N-chloroacetyl, N-trichloroacetyl, N-trifluoroacetyl, N-phenylacetyl, N-3-pyridylcarboxamide, and N-benzoyl.

Carboxyl protecting groups ("J") include substituted methyl esters, 2-substituted ethyl esters, substituted benzyl esters, silyl esters, and activated esters. Examples include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, alpha-methylphenacyl, p-methoxyphenacyl, carboxamidomethyl, N-phthalimidomethyl, 2,2,2-trichloroethyl, 2-haloethyl, omega-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, methylcinnamyl, phenyl, p-(methylmercapto)phenyl, benzyl, triphenylmethyl, diphenylmethyl, bis(o-nitrophenyl)methyl, 9-anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, piperonyl, 4-picolyl, trimethylsilyl, triethylsilyl, t-butyldimethylsilyl, i-propyldimethylsilyl, phenyldimethylsilyl, di-t-butylmethylsilyl, and thiols.

Aryls include aromatic rings, substituted or unsubstituted, preferably having between 6 and 15 carbon atoms, and more preferably between 6 and 12 carbon atoms. Examples of aryls include as phenyl, naphthyl, and indene, pentalene, anthracene, azulene, and biphenylene. Alkylaryls include tolyl, xylyl, mesityl, cumenyl, 2-ethyl-4 methylphenyl. Arylalkyls include benzyl, phenylethyl, and arylenes include 1,4-phenylene.

Except where otherwise specifically defined, e.g., for "Y," heterocyclic radicals may be aromatic (heteroaryl) or nonaromatic, and substituted or unsubstituted. Preferably, they have between 1 and 2 rings, are single, fused or bridged rings, and contain between 2 and 15 carbon atoms in the ring, i.e., exclusive of substitution. Heterocycles include thienyl, furyl, pyranyl, isobenzofuranyl, 2H-pyrrolyl, pyrrolyl, imidazolyl, pyrazolyl, isothiazolyl, oxadiazolyl, oxazolyl, thiadiazolyl, thiazolyl, isoxazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzainyl, furazanyl, pyrrolinyl, pyrrolidinyl, imidazolidinyl, imidazolinyl, piperidyl, piperazinyl, and morpholinyl.

Substituting moieties have one, two, three, or more of the following moieties (instead of a hydrogen): alkyl, alkenyl, alkoxy, aryloxy, alkenyloxy, haloalkyl, haloalkoxy, hydroxy, nitro, chloro, fluoro, bromo, and iodo. In some embodiments, substituting moieties include thiol, cyano, and amino. Preferably, substituting moieties have between 1 and 6 carbon atoms, and more preferably between 1 and 3 carbon atoms, if any. Examples of carbon-containing substitutions include chloromethyl, hydroxymethyl, bromoethyl, methoxy, and ethoxy. An alkyl does not have an alkyl or haloalkyl substituent, although a cycloalkyl may have an alkyl or haloalkyl substituent.

The enzyme inhibitor is preferably a competitive inhibitor. Inhibition is measured by methods known to those in the art and is variously expressed as $K_i$ (molar), $k_{inact}/K_i$ $M^{-1}$ $s^{-1}$, or percent inhibition (relative to absence of inhibitor compound). Preferably, percent inhibition is at least 25%, e.g., at least 30%, or at least 40%, and preferably a $K_i$ in the nM range. Suicide inhibitors or mechanism-based inhibitors are modified by the enzyme, generating a reactive functionality that forms a covalent bond with the target.

Figure 2:
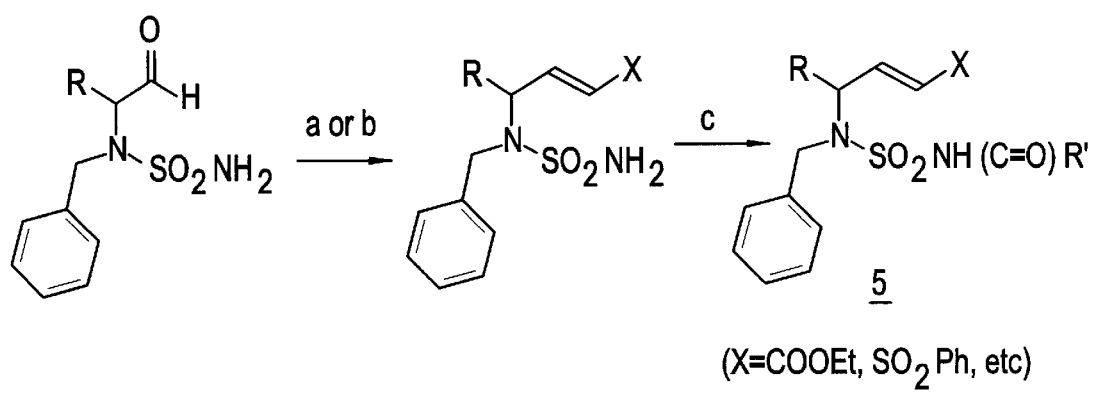
FIG. 2 shows a general reaction scheme for the preparation of cysteine inhibitors. Script below the drawing refers to reagents used to obtain the desired chemical reaction or purification step.
Figure 3:
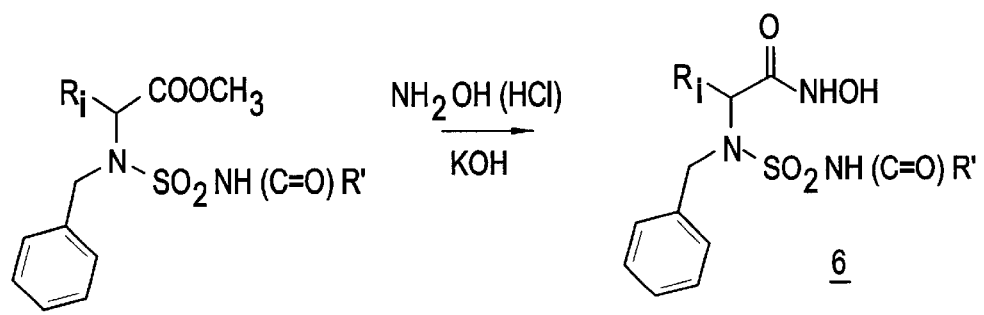
FIG. 3 shows a general reaction scheme for the preparation of MMP protease inhibitors.
Figure 12:
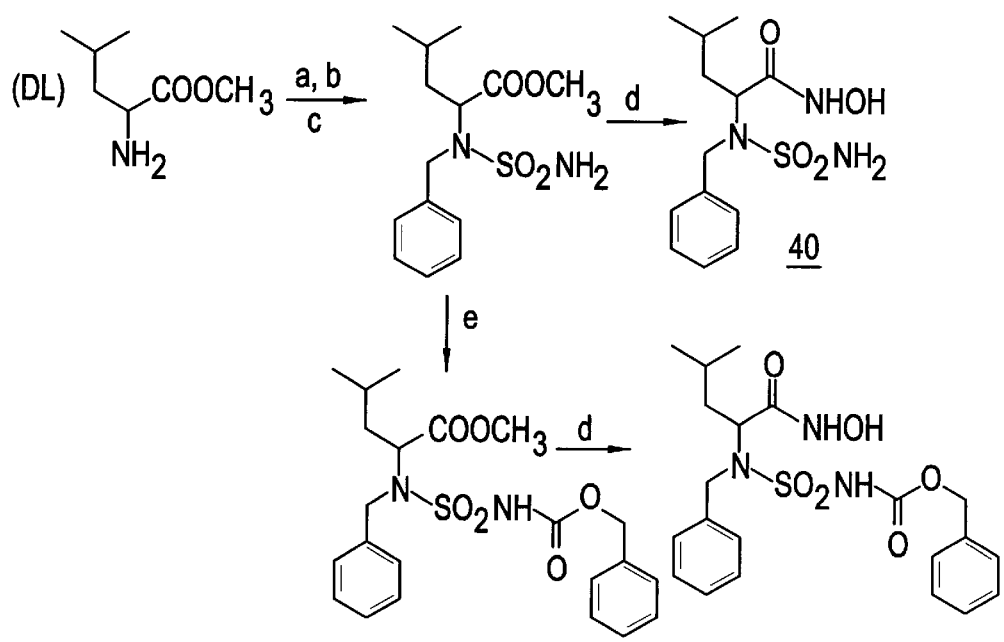
FIG. 12 shows a reaction sequence for the preparation of inhibitor 40. Script below the drawing refers to reagents used to obtain the desired chemical reaction or purification step.

The preparation of the compounds of the invention is straightforward. For example, the compounds may be prepared using an amino acid as the starting compound, in which the amino acid side group is appropriate for the Z-group of the final compound. The carboxyl group of the amino acid may be functionalized to provide the desired Y-group using known methods; and the amino group may be reacted with substituted sulfamoyl chlorides to form the corresponding sulfamide having the desired substitutions for $R_5$ and $R_6$, or having a reactive substrate for further reaction. The nitrogen bearing the "$CR_2YZ$" moiety may be alkylated using well-known methods such as reaction with benzyl and alkyl halides to obtain the desired $R_3$ and $R_4$ groups. FIGS. 1, 2, and 3 illustrate exemplary reaction schemes for the formation of serine, cysteine and MMP protease inhibitors representative of the compounds of formula III and IV. In FIG. 1, compounds 1–4 are potential serine protease inhibitors. Compound 2 can also inhibit cysteine proteases. FIG. 2 illustrates further modifications of the Y-group leading to compound 5, a potential cysteine protease inhibitor. FIG. 3 illustrates formation of a potential MMP inhibitor compound 6. FIG. 12 illustrates the formulation of a compound of formula V, the syntheses of which is described in Example 4.

Figure 5:
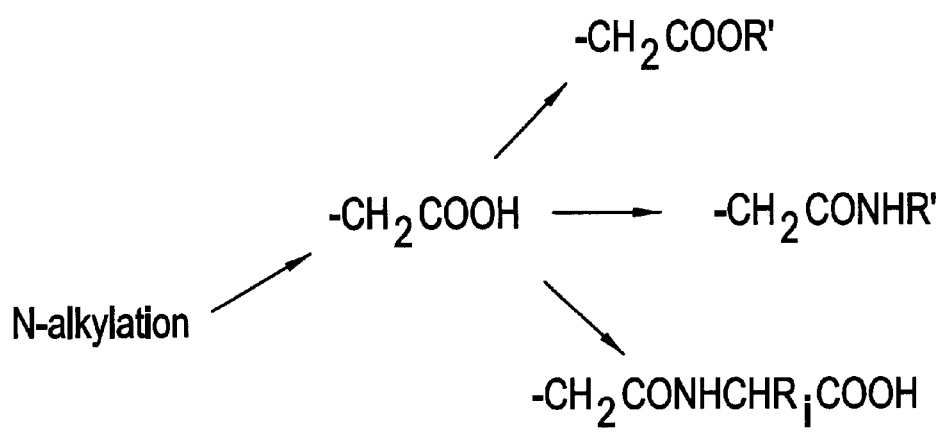
FIG. 5 shows general reaction scheme for the functionalization of a terminal carboxyl group.
Figure 6:
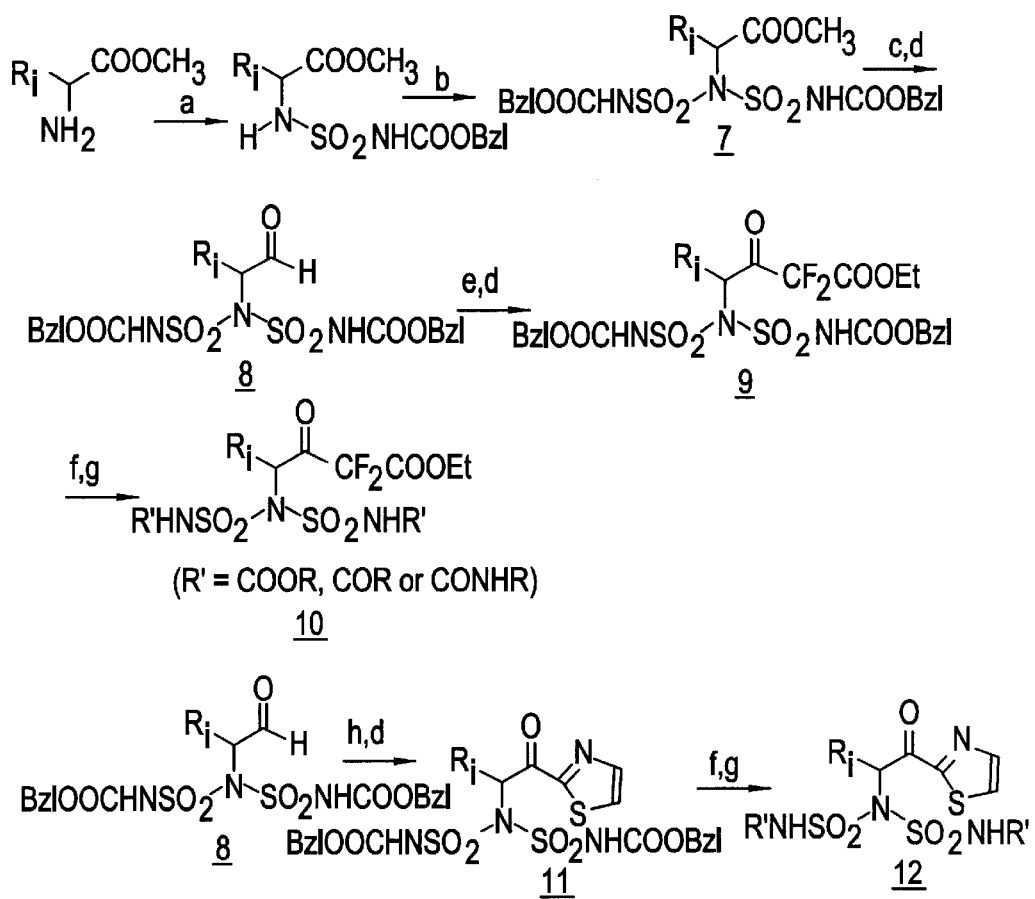
FIG. 6 shows a general reaction scheme for the preparation of bis-sulfamides.

Formation of bis-sulfamide compound VI is illustrated in FIG. 6. Selection of the starting amino acid is made to obtain the desired Z-group in the final compound. The bis-sulfamide is formed by addition of two sulfamide moieties to the amine group of the starting amino acid. Reactions at the amino acid carboxylic acid group are carried out as described above to obtain the desired Y-group. Compounds 8 through 12 are potential serine inhibitors, while compound 8 may be a cysteine inhibitor. Note that intermediate 7 may be used to make MMP inhibitors by reaction with $NH_2OH$. Modification of the compound using conventional carboxylic acid and amino chemistry, such as illustrated in FIGS. 4 and 5, allow the formation of a variety of substituted bis-sulfamides.

Figure 4:
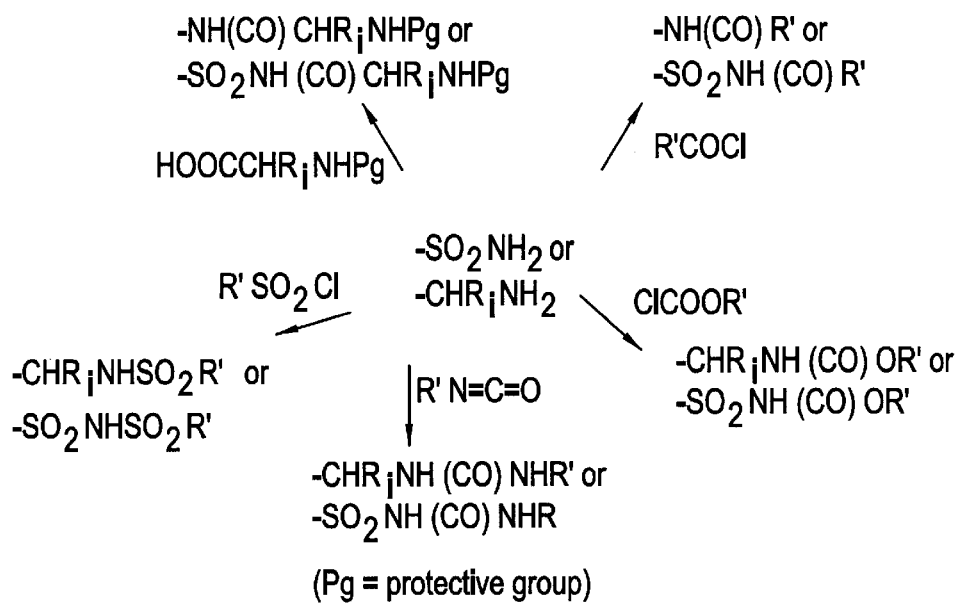
FIG. 4 shows general reaction scheme for the functionalization of a terminal amino or SO$_2$NH$_2$ group.

Functionalization of the compounds of formulae I–VI may be carried out as shown in FIGS. 4 and 5.

For example, when $R_4=CHR_iNH_2$, the pendant amino groups of compounds I and II may be further modified using conventional nucleophilic substitution reactions as shown in FIG. 4, to obtain the corresponding sulfonamides, carbamates, amides, and the like. As is also illustrated in FIG. 4, a sulfamide ($SO_2NH_2$) may be similarly reacted to provide the functional derivatives for $R_{31}$ of compounds III and VI and $R_{34}$ of compounds IV and V.

By way of further example, a nitrogen of the N—$SO_2$—N backbone may be alkylated using bromoacetic acid to obtain the pendant "$CH_2COOH$" of the compounds of formula I and II. The acetic acid moiety may be functionalized using conventional nucleophilic aryl substitution reactions, such as shown in FIG. 5, to obtain the corresponding esters, amides and amino acid condensates.

Figure 10:
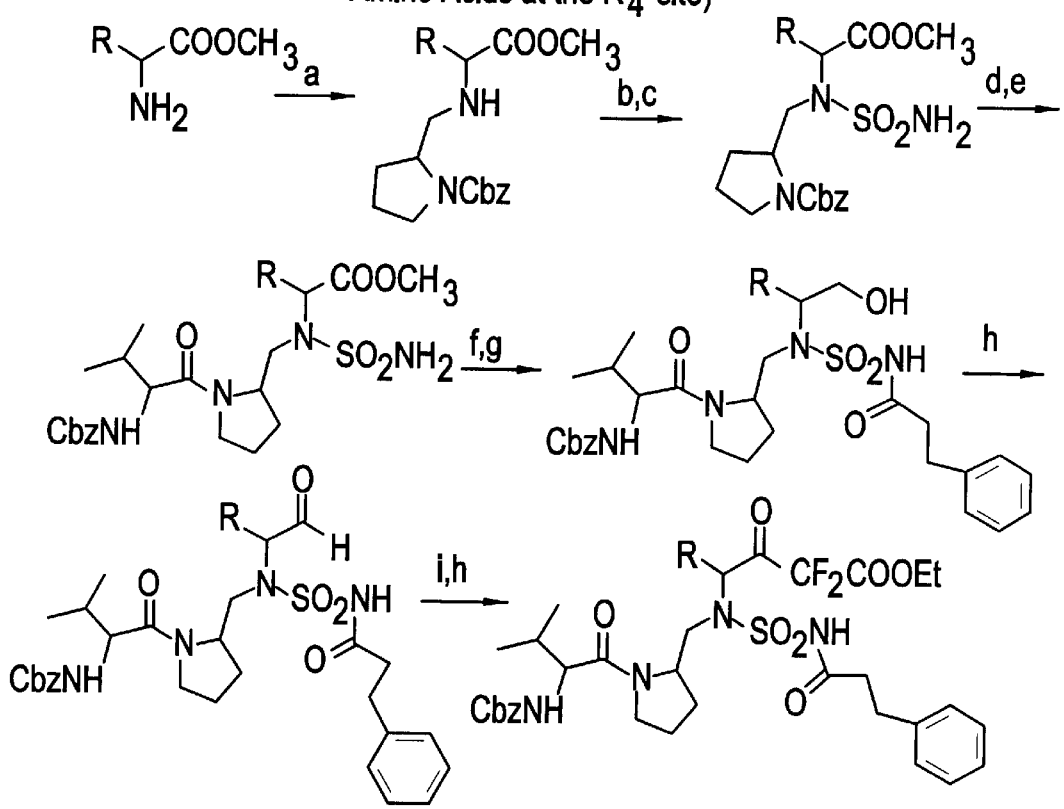
FIG. 10 is a scheme for the chemical synthesis of sulfamide compounds of the invention comprising one or more N-protected amino acids at the $R_4$ site, and which additionally provides a compound of formula V.
Figure 11:
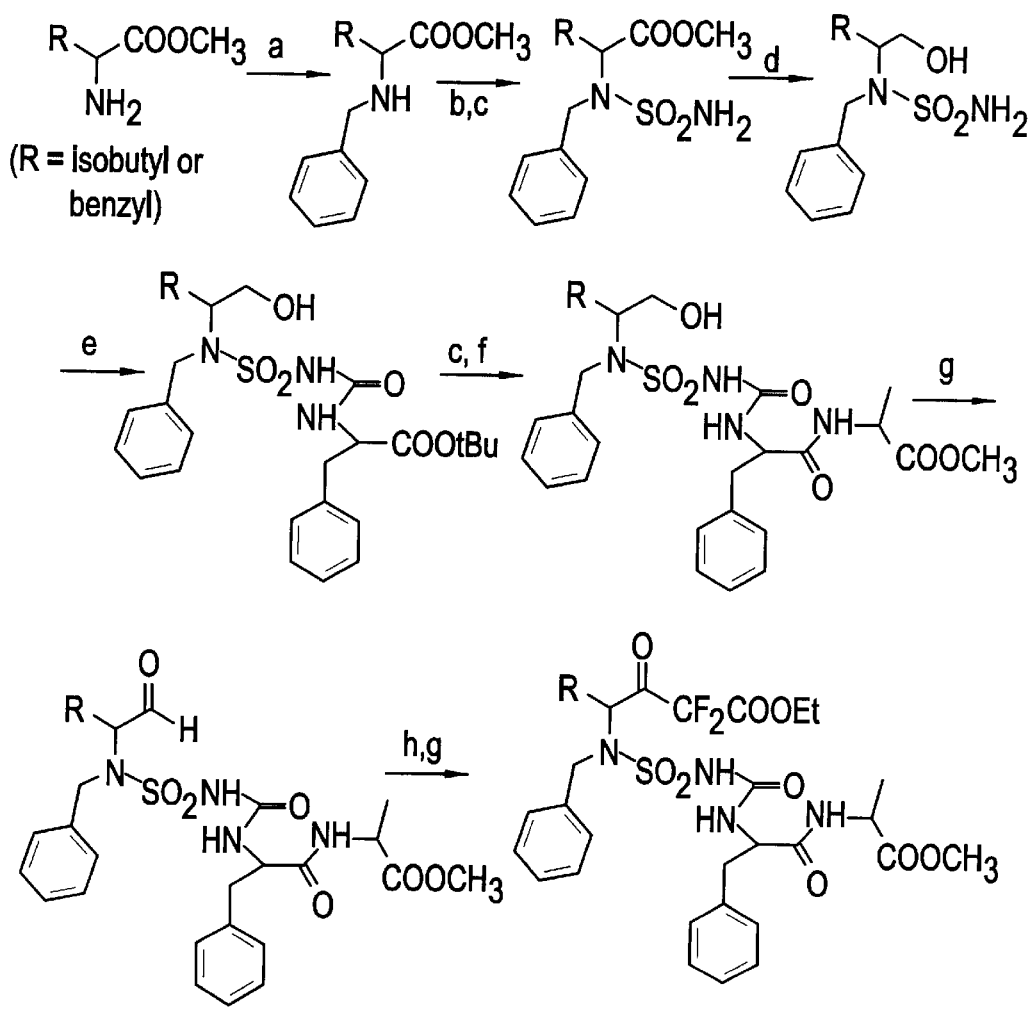
FIG. 11 is a scheme for the chemical synthesis of sulfamide compounds of the invention comprising one or more C-protected amino acids at the $R_6$ site, and which additionally provides for a compound of formula IV.

Standard peptide synthetic techniques may be used in the preparation of pendant groups containing multiple amino acids. For example, the compound of formulae I–VI may be covalently linked to an amino acid residue(s) or peptidomimetic reactant having an isocyanate, chloroformate, hydroxyl, or preferably amino, activated amino, carboxyl, or activated carboxyl functional group. The resulting linking moiety may be urea, urethane, ester and preferably amide linkages. By way of further example, for compounds I and II where $R_4$ and $R_6$ are both carboxyl-terminated, protection of one of $R_4$ and $R_6$ with t-butyl and the other with benzyl allows selective elaboration of each carboxyl group. Similarly, standard Boc and Cbz chemistry is used where $R_4$ and $R_6$ are both amino-terminated, the former being removed by TFA and the latter being removed by catalytic hydrogenation. Exemplary reaction schemes are shown in FIGS. 10 and 11 for the addition to the terminal end of $R_4$ and $R_6$, respectively.

The invention is illustrated by the following examples which are not to be considered limiting of the invention.

I. PREPARATION OF COMPOUNDS

EXAMPLE 1

Preparation of N-benzyl-N-(1-formyl-3-methylbutyl)-N',N'-dimethylfulfamide (15)

Figure 7:
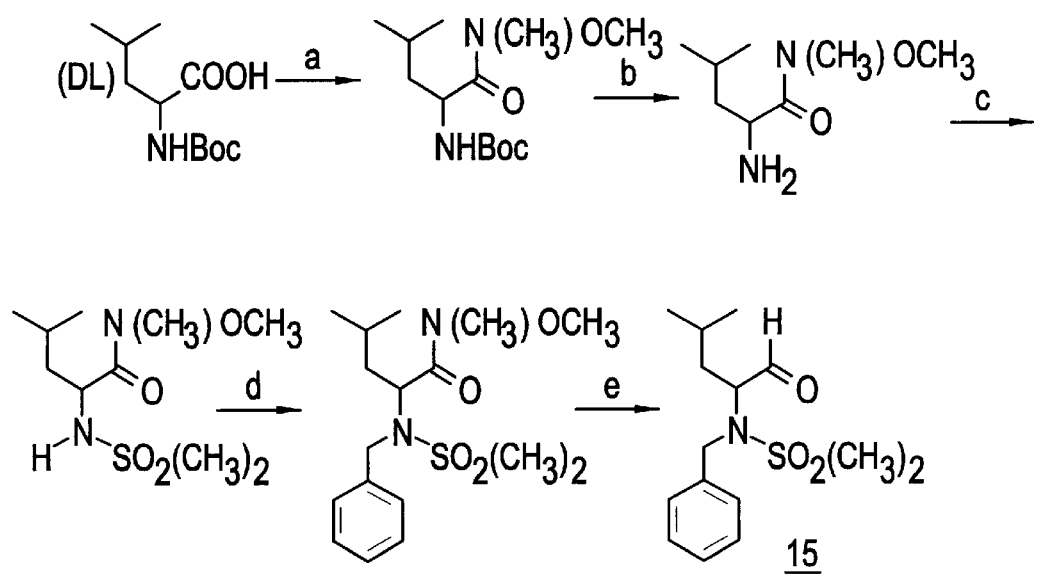
FIG. 7 shows a reaction sequence for the preparation for inhibitor 15, in which Z is an isobutyl moiety derived from leucine. It will be apparent that the starting reagent may be another amino acid so that the Z-position of the final compound may be modified. Script below the drawing refers to reagents used to obtain the desired chemical reaction or purification step.

Compound 15 was prepared according to the reaction scheme 5 shown in FIG. 7, corresponding to the compound of formula I in which Z=isobutyl, Y=CHO, $R_2=R_4$=H, $R_4$=benzyl, $R_5=CH_3$ and $R_6$=H.

Boc-DL-leucine (2.49 g, 10 mmol) was dissolved in dry tetrahydrofuran (THF) under nitrogen, and carbonyl diimidazole (1.62 g, 10 mmol) was added in one portion. N,O-Dimethylhydroxylamine hydrochloride (1.12 g, 11 mmol) was then added followed by triethylamine (1.12 g, 11 mmol). The reaction mixture was stirred at room temperature overnight. The solvent was removed and the residue was treated with ether (125 mL) and water (45 mL). The layers were separated and the organic phase was washed with 5% HCl (3×30 mL), saturated $NaHCO_3$ (3×30 mL) and brine (3×30 mL). The organic phase was then dried and the solvent removed, yielding a pure product (2.50 g, 91% yield).

The product obtained above (2.5 g) was treated with excess $CF_3COOH$ (TFA) and stirred at room temperature for 0.5 h. Removal of excess TFA left a crude TFA salt product which was used in the next step.

The TFA salt (27 mmol) was dissolved in chloroform (60 mL) and treated with triethylamine (8.18 g, 81 mmol) and N,N-dimethylsulfamoyl chloride (4.26 g, 29.7 mmol). The mixture was refluxed for 12 h and allowed to cool to room temperature. The solvent was removed and the residue was treated with ether (150 mL) and water (50 mL). The organic phase was separated and washed with 5% HCl (2×40 mL), 5% $NaHCO_3$ (2×40 mL) amd brine (40 mL). The organic layer was dried using anhydrous sodium sulfate and evaporated to yield a crude product which was purified by flash chromatography using silica gel and hexane/ether as eluents (2.0 g, 26% yield).

The sulfamide derivative (1.193 g, 6.73 mmol) obtained above was dissolved in dry acetonitrile (15 mL) and sodium hydride (0.35 g, 8.75 mmol) was added in several portions. Benzyl bromide (1.61 g, 9.4 mmol) was added and the reaction mixture was stirred for 16 h at room temperature. The solvent was removed and the residue was treated with ether (75 mL) and water (25 mL). The organic phase was washed with brine (20 mL) and dried over anhydrous sodium sulfate. Removal of the solvent left a crude product which was purified by flash chromatography using a hexane/ether gradient as eluents (1.50 g, 60% yield). $^1$H NMR ($CDCl_3$): 0.5 (d,3H), 0.9 (d,3H), 1.4 (m,2H), 1.65 (m,1H), 2.68 (s,6H), 3.18 (s,3H), 3.72 (s,3H), 4.90 (m,3H), 7.2–7.33 (m,3H), 7.43 (m,2H).

A solution of the product obtained above (0.38 g, 1 mmol) in dry ether (10 mL) was cooled to 0° C. and kept under nitrogen. Lithium aluminum hydride (38 mg) was added in one portion and the reaction mixture w as stirred for 20 minutes at 0° C. The mixture was poured into a solution of $KHSO_4$ (0.5 g/10 mL water). The organic phase was separated and washed with 5% HCl (2×10 mL), saturated $NaHCO_3$ (2×10 mL) and brine (10 mL). The organic phase was dried and then evaporated, leaving a crude product which was purified by flash chromatography (silica gel/hexane/ether gradient) to yield 0.15 g (48% yield) of pure compound 1. $^1$H NMR ($CDCl_3$): 0.87 (dd,6H), 1.58 (m,1H), 1.7 (m,1H), 1.82 (m,1H), 2.86 (s,6H), 3.93 (t,1H), 4.29 (dd,2H), 7.34 (m,5H), 9.48 (s,1H). $^{13}$C NMR ($CDCl_3$): 199.78, 64.47.

EXAMPLE 2

Preparation of $N^2$-benzyl-$N^2$-[(dimethylamino)sulfonyl]-$N^1$-hydroxyglycinabmide (20)

Figure 8:
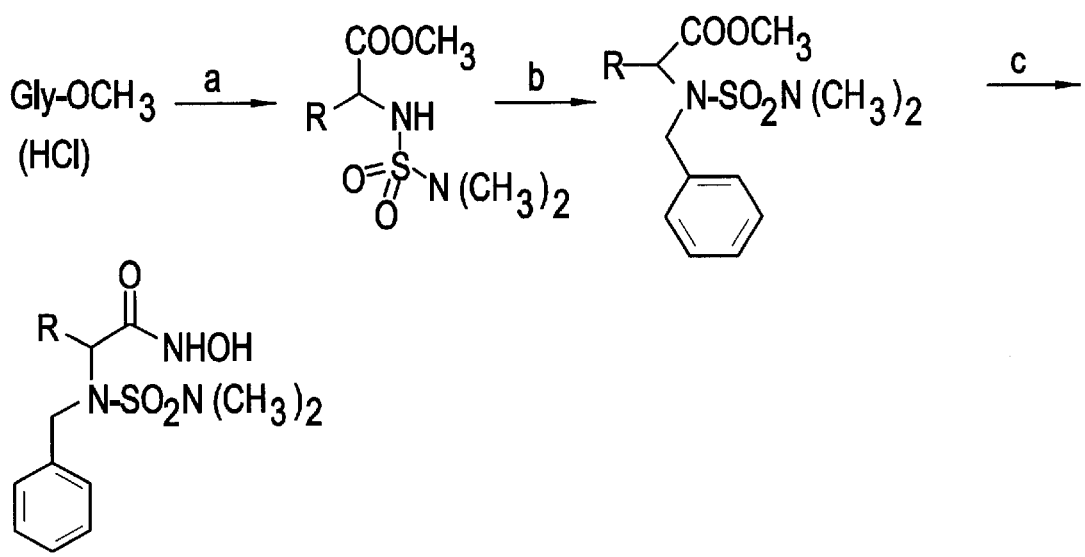
FIG. 8 shows a reaction sequence for the preparation of inhibitor 20 and 30 in which Z is an hydrogen moiety derived from glycine for compound 20 and Z is an isopropyl moiety derived from valine for compound 30. Script below the drawing refers to reagents used to obtain the desired chemical reaction or purification step.
Figure 9:
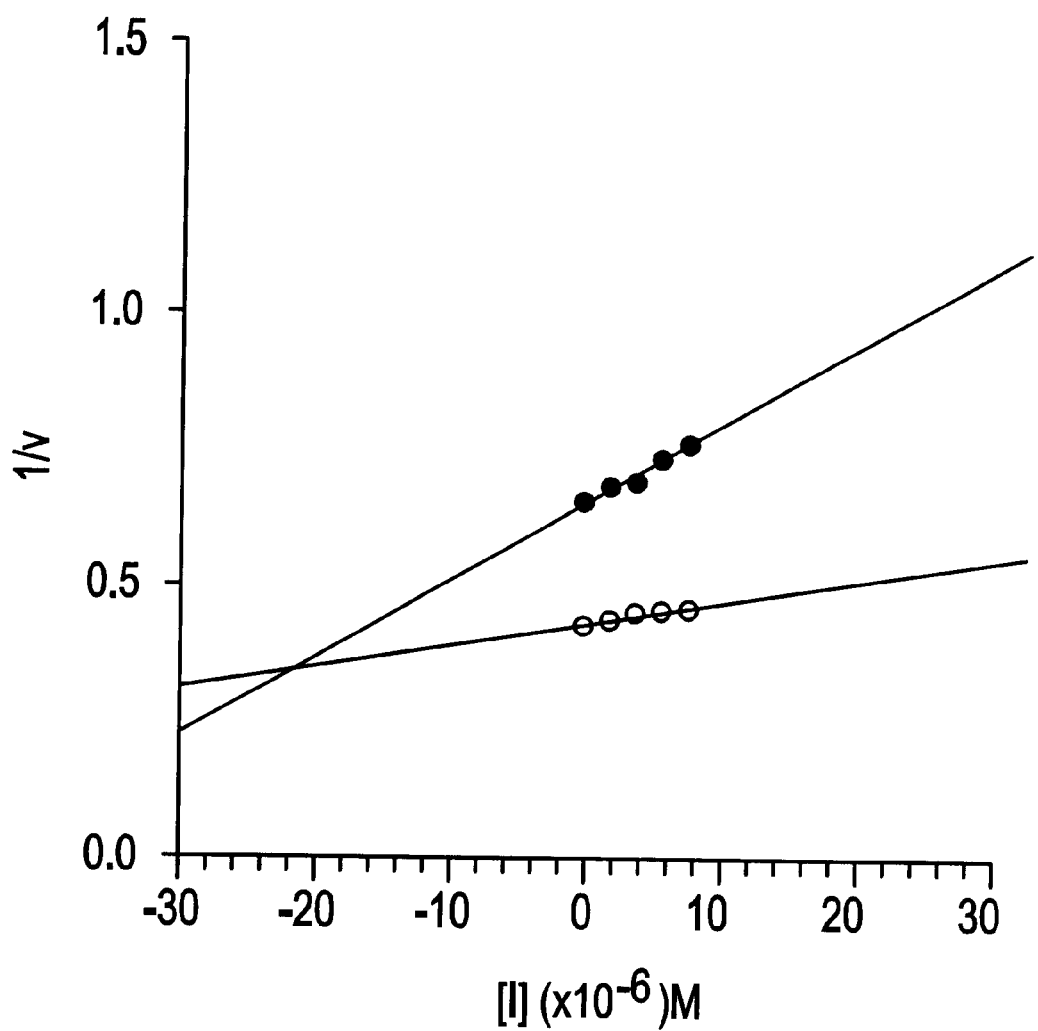
FIG. 9 shows a Dixon plot for the inhibition of human leukocyte elastase (HLE) by compound 15.

Compound 20 was prepared according to the reaction scheme 6 shown in FIG. 8, corresponding to the compound of formula I in which Z=H, Y=(CO)NHOH, $R_2=R_4$=H, $R_4$=benzyl, $R_5=CH_3$ and $R_6$=H.

Glycine methyl ester hydrochloride (2.5 g, 20 mmol) and triethylamine 5.26 g, 52 mmol) in methylene chloride (20 mL) were reacted with dimethylsulfamoyl chloride (3.7 g, 26 mmol) at room temperature. After stirring or 1 h, 4-dimethylamino pyridine (DMAP) (2.0 g) was added and stirring was continued for an additional hour. The solvent was removed in vacuo and the residue was taken up in ethyl acetate (40 mL) and washed with 5% HCl and brine. It was then dried over anhydrous sodium sulfate. Removal of the solvent left a pure product (3.4 g, 87% yield), which was used in the next step without further purification. $^1$H NMR ($CDCl_3$): 2.81 (s,6H), 3.79 (s,3H), 3.87 (d,2H), 5.10 (br t, 1H). $^{13}$C NMR ($CDCl_3$): 37.83, 44.48, 52.42, 170.04.

A mixture of the compound obtained above (2.0 g, 10 mmol) and benzyl bromide (2.0 g, 11.7 mmol) in dry acetonitrile (10 mL) kept at 0° C. was treated with 60% sodium hydride (0.6 g, 14.9 mmol). The reaction mixture was stirred for thirty minutes at 0° C. and 2 h at room temperature. The solvent was then removed and the residue was taken up in ethyl acetate. Work up as above yielded a product which was purified by flash chromatography using silica gel and hexane/ethyl acetate as eluents (2.5 g, 90% yield). $^1$H NMR ($CDCl_3$): 2.87 (s,6H), 3.70 (s,3H), 3.85 (s,2H), 4.55 (s,2H), 7.33 (m,5H).

Finely ground hydroxyamine hydrochloride (0.16 g, 2.3 mmol) in 3 mL ethanol was mixed with a solution of potassium hydroxide (0.25 g, 4 mmol) in 3 mL ethanol at 0° C. The precipitate was filtered off and the filtrate was added to a solution of the ester (0.57 g, 2 mmol) obtained above in 3 mL ethanol at 0° C. The resulting solution was stirred at room temperature overnight. The solvent was removed in vacuo and the residue was treated with 5% HCl and extracted with ethyl acetate (3×20 mL). The organic extracts were combined, dried and evaporated. The crude product was purified by flash chromatography using silica gel and a hexane/ethyl acetate/10% methanol gradient (0.35 g, 61% yield). $^1$H NMR ($CDCl_3$): 2.78 (s,6H), 3.75 (s,2H), 4.44

(s,2H), 7.31 (m,5H). $^{13}$C NMR (CDCl$_3$): 37.91, 47.70, 52.89, 128.22, 128.61, 128.79, 135.20, 166.69.

EXAMPLE 3

Preparation of $N^2$-[(dimethylamino)sulfonyl]-$N^1$-hydroxy-$N^2$-(2-methyl-1-phenylpropyl)glycinamide (30)

Compound 30 was prepared as described above for compound 20 as shown in FIG. 8 except that D-valine methyl ester hydrochloride was used as the starting material, corresponding to the compound of formula I in which Z=isobutyl, Y=CHO, $R_2$=$R_4$=H, $R_4$=benzyl, $R_5$=CH$_3$ and $R_6$=H.

EXAMPLE 4

Preparation of $N^2$-(aminosulfonyl-$N^2$-benzyl-$N^1$-hydroxyleucinamide (40)

Compound 40 was prepared according to the reaction scheme shown in FIG. 12, corresponding to the compound of formula IV in which Z=isobutyl, Y=CHNHOH, $R_{30}$=H, $R_{34}$=benzyl; and $R_{35}$=CH$_2$Ph.

A mixture of (DL) Leucine methyl ester hydrochloride (2.18 g; 14.34 mmol), in 1,2 dichloroethane (30 mL) was treated with benzaldehyde (1.52 g; 14.34 mmol), glacial acetic acid (0.096 g; 1.62 mmol) and sodium triacetoxyborohydride (3.55 g; 16.8 mmol) under nitrogen. The mixture was stirred at room temperature for 4 h. The pH of the solution was adjusted to ~10 by adding slowly 10% aqueous NaOH while stirring. The organic layer was separated and the aqueous solution was extracted with ethyl acetate (3×25 mL). The organic extracts were combined and dried over anhydrous sodium sulfate. Evaporation of the solvent left an oily product which was purified by flash chromatography using silica gel and hexane/ether eluent (1.88 g; 67% yield). $^1$H NMR(CDCl$_3$): 0.84 (d,3H), 1.4 (t,2H), 1.72 (br s, 1H), 1.80 (m,1H), 3.2 (t.1H), 3.2 (d,1H), 3.70 (s,3H), 3.8 (d,1H), 7.30 (m,5H).

A solution of chlorosulfonyl isocyanate (2.1 g; 14.8 mmol) in dry methylene chloride (25 mL) was cooled in an ice bath and kept under nitrogen. A solution of t-butyl alcohol (1.1 g; 14.8 mmol) in methylene chloride (10 mL) was added dropwise. The resulting solution was transferred to an addition funnel and added dropwise to a solution of N-benzyl-L-leucine methyl ester (3.27 g; 14.8 mmol) and triethylamine (1.50 g; 14.8 mmol) in methylene chloride (30 mL) kept at 0° C. The reaction mixture was stirred at room temperature for 2 h. It was then transferred to a separatory funnel, washed with water (2×25 mL) and dried over .anhydrous sodium sulfate to yield a pure oily product (5.39 g; 88% yield). $^1$H NMR (CDCl$_3$): 0.58 (d,3H), 0.84 (d,3H), 1.60 (s,9H, 3.70 (s,3H), 4.60 (d,1H), 4.64 (t,1H), 4.92 (d,1H), 5.30 (s,2H), 7.22–7.42 (m,5H).

The compound obtained above (6.37 g; 8.57 mmol) was treated with trifluoroacetic acid (22 mL) in methylene chloride (6 mL) and stirred at room temperature for 2 h. Excess trifluoroacetic acid was removed in vacuo and the residue was taken up in methylene chloride (40 mL) and washed with 5% NaHCO$_3$ (2×25 mL) and brine (2×25 mL). The organic layer was dried over anhydrous sodium sulfate and the solvent removed, leaving a crude product which was purified by chromatography using silica gel and hexane/ether eluent. $^1$H NMR(CDCl$_3$): 0.54 (d,3H), 0.75 (d,3H), 1.40–1.70 (m,3H), 3.75 (s,3H), 4.2 (d,1H), 4.4 (t,1H), 4.52 (d,1H), 5.2 (s,2H), 7.22–7.42 (m,5H).

A solution of hydroxylamine hydrochloride (2.5 g; 35 mmol) in absolute ethanol (6 mL) was mixed with a solution of potassium hydroxide (2.0 g; 35 mmol) in absolute ethanol (6 mL) at 0° C. The precipitate was filtered off and the filtrate was added to a solution of methyl N-(aminosulfonyl)-N-benzylleucinate obtained above (2.2 g; 6.9 mmol) in absolute ethanol (6 mL) kept at 0° C. The reaction mixture was stirred at room temperature for 2 h. The solvent was removed in vacuo and the residue was taken up in ethyl acetate (75 mL) ans washed with 5% HCL (25 mL). The aqueous layer was extracted with ethyl acetate (50 mL) and the combined organic extracts were dried over anhydrous sodium sulfate. Removal of the solvent yielded the desired hydroxamic acid which was purified by flash chromatography (1.8 g). $^1$H NMR(CDCl$_3$): 0.78 (d,3H), 0.80 (d,3H), 1.6–1.8 (m,3H), 3.7 (m,3H), 3.95 (t,1H), 4.36 (d,1H), 4.50 (d,1H), 7.4 (s,5H), 9.10 (br s,1H).

II. BIOLOGICAL ACTIVITY

EXAMPLE 5

The inhibitory activity of compound 15 toward HLE was determined under competitive inhibition conditions. The $K_i$ value for compound 1 was determined using a Dixon plot as shown in FIG. 3. (Dixon, M. *Biochem. J.* 20 55:70–71 (1953)). Human leukocyte elastase (HLE assay has been described in detail; see, Groutas et al. *Biochemistry* 36:4739 (1997).

EXAMPLE 6

The inhibitory activity of compound 20 and 30 toward thermolysin was determined under competitive inhibition conditions. Thermolysin activity with or without inhibitor was measured using N-[3-[2-Furyl]acryloyl]-Gly-L-Leu-NH$_2$ as substrate (Walsh, K. A. et al. *Methods Enzymol.*34:435 (1974); Nishino, N. et al. *Biochemistry* 17:2846 (1978)).

Table 3 reports the measured $K_i$ values for compounds 15 and 20 reported in Examples 1 and 2 and % inhibition value for compound 40 reported in Example 4.

TABLE 3

| Compound | Enzyme | $K_1$ or % Inhibition |
| --- | --- | --- |
| 15 | Elastase (HLE) | 21 µM |
| 20 | Thermolysin | 1.2 µM |
| 40 | Thermolysin | 26% inhibition |

What is claimed is:
1. A compound having the formula:

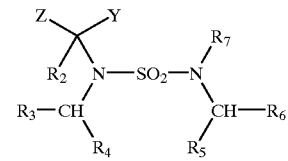

and pharmaceutically acceptable salts thereof, wherein,
Z is a functional group selected from the group consisting of alkyl, branched alkyl, alkylaryl, alkyl amine, carboxylic acid, amide, and guanidinium other than methyl or isopropyl;
Y is a functional group capable of reacting with zinc or a basic sulfhydryl group of an active site cysteine;

$R_2$, $R_3$, $R_5$ and $R_7$ are each independently selected from the group consisting hydrogen, alkyls, aryls, substituted aryls, alkylaryls and arylalkyls; and $R_4$ and $R_6$ are each independently selected from the group consisting of H, alkyl, aryl, arylalkyl, a functional group having the formula —C(O)—, and substituted derivatives thereof, wherein the carbon to which $R_2$, Z and Y are bonded is chiral.

2. A compound according to claim 1 wherein Z is a functional group selected from the group consisting of benzyl, ethyl, isobutyl, n-propyl, $(CH_2)_4NH_2$, $(CH_2)_3(C=NH)NH_2$, and $CH_2COOH$.

3. A compound having the formula:

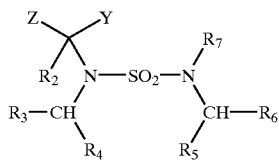

and pharmaceutically acceptable salts thereof, wherein,

Z is a functional group selected from the group consisting of alkyl, branched alkyl, alkylaryl, alkyl amine, carboxylic acid, amide, and guanidinium other than methyl or isopropyl;

Y is a functional group selected from the group consisting of functional groups having the formula —C(O)—, functional groups having the formula —CH=CH(CO)—, and functional groups having the formula —CH=CHSO_2—;

$R_2$, $R_3$, $R_5$ and $R_7$ are each independently selected from the group consisting hydrogen, alkyls, aryls, substituted aryls, alkylaryls and arylalkyls; and $R_4$ and $R_6$ are each independently selected from the group consisting of H, alkyl, aryl, arylalkyl, a functional group having the formula —C(O)—, and substituted derivatives thereof, wherein the carbon to which $R_2$, Z and Y are bonded is chiral.

4. A compound according to claim 3 wherein Z is a functional group selected from the group consisting of benzyl, ethyl, isobutyl, n-propyl, $(CH_2)_4NH_2$, $(CH_2)_3(C=NH)NH_2$, and $CH_2COOH$.

5. A compound according to claim 3 wherein Y is a functional group selected from the group consisting of $C(O)CF_3$, $C(O)CF_2C(O)OEt$, $C(O)_2$-benzoxazole, $C(O)_2$-thiazole, $C(O)$oxadiazole, CH=CH(CO)OEt, CH=CHSO_2CH_3, CH=CHSO_2Ph, (CO)CH_2F, CHO, C(O)NHOH.

6. A compound having the formula:

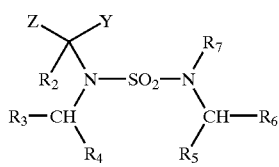

and pharmaceutically acceptable salts thereof, wherein, is a functional group selected from the group consisting of alkyl, branched alkyl, alkylaryl, alkyl amine, carboxylic acid, amide, and guanidinium;

Y is a functional group capable of reacting with zinc or a basic sulfhydryl group of an active site cysteine;

$R_2$, $R_3$, $R_5$ and $R_7$ are each independently selected from the group consisting hydrogen, alkyls, aryls, substituted aryls, alkylaryls and arylalkyls; and $R_4$ and $R_6$ are each independently selected from the group consisting of H, alkyl, aryl, arylalkyl, a functional group having the formula —C(O)—, and substituted derivatives thereof, wherein the carbon to which $R_2$, Z and Y are bonded is chiral; and at least one of $R_4$ and $R_6$ is an alkyl amine or has a functional group having the formula —C(O)—.

7. A compound according to claim 6 wherein Z is a functional group selected from the group consisting of benzyl, ethyl, isobutyl, n-propyl, $(CH_2)_4NH_2$, $(CH_2)_3(C=NH)NH_2$, and $CH_2COOH$.

8. A compound having the formula:

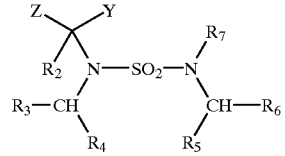

and pharmaceutically acceptable salts thereof, wherein,

Z is a functional group selected from the group consisting of alkyl, branched alkyl, alkylaryl, alkyl amine, carboxylic acid, amide, and guanidinium;

Y is a functional group selected from the group consisting of functional groups having the formula —C(O)—, functional groups having the formula —CH=CH(CO)—, and functional groups having the formula —CH=CHSO_2—;

$R_2$, $R_3$, $R_5$ and $R_7$ are each independently selected from the group consisting hydrogen, alkyls, aryls, substituted aryls, alkylaryls and arylalkyls; and $R_4$ and $R_6$ are each independently selected from the group consisting of H, alkyl, aryl, arylalkyl, a functional group having the formula —C(O)—, and substituted derivatives thereof, wherein the carbon to which $R_2$, Z and Y are bonded is chiral; and at least one of $R_4$ and $R_6$ is an alkyl amine or has a functional group having the formula —C(O)—.

9. A compound according to claim 8 wherein Z is a functional group selected from the group consisting of benzyl, ethyl, isobutyl, n-propyl, $(CH_2)_4NH_2$, $(CH_2)_3(C=NH)NH_2$, and $CH_2COOH$.

10. A compound according to claim 8 wherein Y is a functional group selected from the group consisting of $C(O)CF_3$, $C(O)CF_2C(O)OEt$, $C(O)_2$-benzoxazole, $C(O)_2$-thiazole, $C(O)$oxadiazole, CH=CH(CO)OEt, CH=CHSO_2CH_3, CH=CHSO_2Ph, (CO)CH_2F, CHO, C(O)NHOH.

11. A compound having the formula:

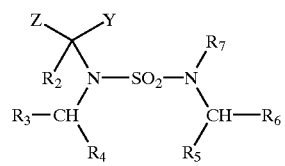

and pharmaceutically acceptable salts thereof, wherein,

Z is a functional group selected from the group consisting of alkyl, branched alkyl, alkylaryl, alkyl amine, carboxylic acid, amide, and guanidinium;

Y is a functional group capable of reacting with zinc or a basic sulfhydryl group of an active site cysteine;

$R_2$, $R_3$, $R_5$ and $R_7$ are each independently selected from the group consisting hydrogen, alkyls, aryls, substituted aryls, alkylaryls and arylalkyls; and $R_4$ and $R_6$ are each independently selected from the group consisting of H, alkyl, aryl, arylalkyl, a functional group having the formula —C(O)—, and substituted derivatives thereof, wherein the carbon to which $R_2$, Z and Y are bonded is chiral; and $R_5$, $R_6$, and $R_7$ taken together does not form —N(CH$_3$)$_2$.

12. A compound according to claim 11 wherein Z is a functional group selected from the group consisting of benzyl, ethyl, isobutyl, n-propyl, (CH$_2$)$_4$NH$_2$, (CH$_2$)$_3$(C=NH)NH$_2$, and CH$_2$COOH.

13. A compound having the formula:

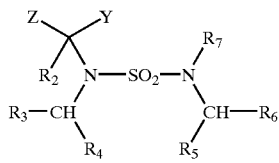

and pharmaceutically acceptable salts thereof, wherein,

Z is a functional group selected from the group consisting of alkyl, branched alkyl, alkylaryl, alkyl amine, carboxylic acid, amide, and guanidinium;

Y is a functional group selected from the group consisting of functional groups having the formula —C(O)—, functional groups having the formula —CH=CH(CO)—, and functional groups having the formula —CH=CHSO$_2$—;

$R_2$, $R_3$, $R_5$ and $R_7$ are each independently selected from the group consisting hydrogen, alkyls, aryls, substituted aryls, alkylaryls and arylalkyls; and $R_4$ and $R_6$ are each independently selected from the group consisting of H, alkyl, aryl, arylalkyl, a functional group having the formula —C(O)—, and substituted derivatives thereof, wherein the carbon to which $R_2$, Z and Y are bonded is chiral; and $R_5$, $R_6$, and $R_7$ taken together does not form —N(CH$_3$)$_2$.

14. A compound according to claim 13 wherein Z is a functional group selected from the group consisting of benzyl, ethyl, isobutyl, n-propyl, (CH$_2$)$_4$NH$_2$, (CH$_2$)$_3$(C=NH)NH$_2$, and CH$_2$COOH.

15. A compound according to claim 13 wherein Y is a functional group selected from the group consisting of C(O)CF$_3$, C(O)CF$_2$C(O)OEt, C(O)$_2$-benzoxazole, C(O)$_2$-thiazole, C(O)oxadiazole, CH=CH(CO)OEt, CH=CHSO$_2$CH$_3$, CH=CHSO$_2$Ph, (CO)CH$_2$F, CHO, C(O)NHOH.

16. A method for reducing or inhibiting the activity of a protease, the method comprising:

contacting said protease with a compound having the formula:

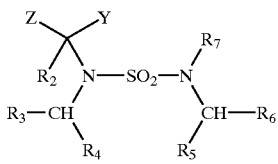

and pharmaceutically acceptable salts thereof, wherein,

Z is a functional group selected from the group consisting of alkyl, branched alkyl, alkylaryl, alkyl amine, carboxylic acid, amide, and guanidinium other than methyl or isopropyl;

Y is a functional group capable of reacting with zinc or a basic sulfhydryl group of an active site cysteine;

$R_2$, $R_3$, $R_5$ and $R_7$ are each independently selected from the group consisting hydrogen, alkyls, aryls, substituted aryls, alkylaryls and arylalkyls; and $R_4$ and $R_6$ are each independently selected from the group consisting of H, alkyl, aryl, arylalkyl, a functional group having the formula —C(O)—, and substituted derivatives thereof, wherein the carbon to which $R_2$, Z and Y are bonded is chiral.

17. A method according to claim 16 wherein Z is a functional group selected from the group consisting of benzyl, ethyl, isobutyl, n-propyl, (CH$_2$)$_4$NH$_2$, (CH$_2$)$_3$(C=NH)NH$_2$, and CH$_2$COOH.

18. A method for reducing or inhibiting the activity of a protease, the method comprising:

contacting said protease with a compound having the formula:

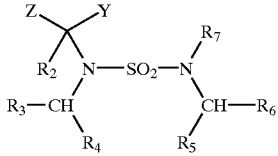

and pharmaceutically acceptable salts thereof, wherein,

Z is a functional group selected from the group consisting of alkyl, branched alkyl, alkylaryl, alkyl amine, carboxylic acid, amide, and guanidinium other than methyl or isopropyl;

Y is a functional group selected from the group consisting of functional groups having the formula —C(O)—, functional groups having the formula —CH=CH(CO)—, and functional groups having the formula —CH=CHSO$_2$—;

$R_2$, $R_3$, $R_5$ and $R_7$ are each independently selected from the group consisting hydrogen, alkyls, aryls, substituted aryls, alkylaryls and arylalkyls; and $R_4$ and $R_6$ are each independently selected from the group consisting of H, alkyl, aryl, arylalkyl, a functional group having the formula —C(O)—, and substituted derivatives thereof, wherein the carbon to which $R_2$, Z and Y are bonded is chiral.

19. A method according to claim 18 wherein Z is a functional group selected from the group consisting of benzyl, ethyl, isobutyl, n-propyl, (CH$_2$)$_4$NH$_2$, (CH$_2$)$_3$(C=NH)NH$_2$, and CH$_2$COOH.

20. A method according to claim 18 wherein Y is a functional group selected from the group consisting of C(O)CF$_3$, C(O)CF$_2$C(O)OEt, C(O)$_2$-benzoxazole, C(O)$_2$- thiazole, C(O)oxadiazole, CH=CH(CO)OEt, CH=CHSO$_2$CH$_3$, CH=CHSO$_2$Ph, (CO)CH$_2$F, CHO, C(O)NHOH.

21. A method for reducing or inhibiting the activity of a protease, the method comprising:
contacting said protease with a compound having the formula:

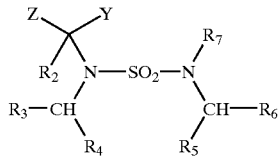

and pharmaceutically acceptable salts thereof, wherein,
Z is a functional group selected from the group consisting of alkyl, branched alkyl, alkylaryl, alkyl amine, carboxylic acid, amide, and guanidinium;
Y is a functional group capable of reacting with zinc or a basic sulfhydryl group of an active site cysteine;
R$_2$, R$_3$, R$_5$ and R$_7$ are each independently selected from the group consisting hydrogen, alkyls, aryls, substituted aryls, alkylaryls and arylalkyls; and
R$_4$ and R$_6$ are each independently selected from the group consisting of H, alkyl, aryl, arylalkyl, a functional group having the formula —C(O)—, and substituted derivatives thereof, wherein
the carbon to which R$_2$, Z and Y are bonded is chiral; and
at least one of R$_4$ and R$_6$ is an alkyl amine or has a functional group having the formula —C(O)—.

22. A method according to claim 21 wherein Z is a functional group selected from the group consisting of benzyl, ethyl, isobutyl, n-propyl, (CH$_2$)$_4$NH$_2$, (CH$_2$)$_3$(C=NH)NH$_2$, and CH$_2$COOH.

23. A method for reducing or inhibiting the activity of a protease, the method comprising:
contacting said protease with a compound having the formula:

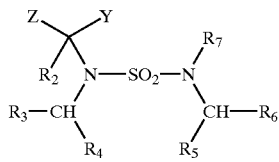

and pharmaceutically acceptable salts thereof, wherein,
Z is a functional group selected from the group consisting of alkyl, branched alkyl, alkylaryl, alkyl amine, carboxylic acid, amide, and guanidinium;
Y is a functional group selected from the group consisting of functional groups having the formula —C(O)—, functional groups having the formula —CH=CH(CO)—, and functional groups having the formula —CH=CHSO$_2$—;
R$_2$, R$_3$, R$_5$ and R$_7$ are each independently selected from the group consisting hydrogen, alkyls, aryls, substituted aryls, alkylaryls and arylalkyls; and
R$_4$ and R$_6$ are each independently selected from the group consisting of H, alkyl, aryl, arylalkyl, a functional group having the formula —C(O)—, and substituted derivatives thereof, wherein
the carbon to which R$_2$, Z and Y are bonded is chiral; and
at least one of R$_4$ and R$_6$ is an alkyl amine or has a functional group having the formula —C(O)—.

24. A method according to claim 23 wherein Z is a functional group selected from the group consisting of benzyl, ethyl, isobutyl, n-propyl, (CH$_2$)$_4$NH$_2$, (CH$_2$)$_3$(C=NH)NH$_2$, and CH$_2$COOH.

25. A compound according to claim 23 wherein Y is a functional group selected from the group consisting of C(O)CF$_3$, C(O)CF$_2$C(O)OEt, C(O)$_2$-benzoxazole, C(O)$_2$-thiazole, C(O)oxadiazole, CH=CH(CO)OEt, CH=CHSO$_2$CH$_3$, CH=CHSO$_2$Ph, (CO)CH$_2$F, CHO, C(O)NHOH.

26. A method for reducing or inhibiting the activity of a protease, the method comprising:
contacting said protease with a compound having the formula:

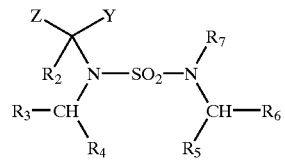

and pharmaceutically acceptable salts thereof, wherein,
Z is a functional group selected from the group consisting of alkyl, branched alkyl, alkylaryl, alkyl amine, carboxylic acid, amide, and guanidinium;
Y is a functional group capable of reacting with zinc or a basic sulfhydryl group of an active site cysteine;
R$_2$, R$_3$, R$_5$ and R$_7$ are each independently selected from the group consisting hydrogen, alkyls, aryls, substituted aryls, alkylaryls and arylalkyls; and
R$_4$ and R$_6$ are each independently selected from the group consisting of H, alkyl, aryl, arylalkyl, a functional group having the formula —C(O)—, and substituted derivatives thereof, wherein
the carbon to which R$_2$, Z and Y are bonded is chiral; and
R$_5$, R$_6$, and R$_7$ taken together does not form —N(CH$_3$)$_2$.

27. A method according to claim 26 wherein Z is a functional group selected from the group consisting of benzyl, ethyl, isobutyl, n-propyl, (CH$_2$)$_4$NH$_2$, (CH$_2$)$_3$(C=NH)NH$_2$, and CH$_2$COOH.

28. A method for reducing or inhibiting the activity of a protease, the method comprising:
contacting said protease with a compound having the formula:

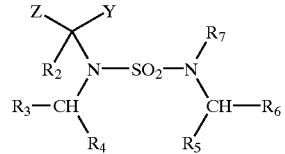

and pharmaceutically acceptable salts thereof, wherein,
Z is a functional group selected from the group consisting of alkyl, branched alkyl, alkylaryl, alkyl amine, carboxylic acid, amide, and guanidinium;
Y is a functional group selected from the group consisting of functional groups having the formula —C(O)—, functional groups having the formula —CH=CH(CO)—, and functional groups having the formula —CH=CHSO$_2$—;

$R_2$, $R_3$, $R_5$ and $R_7$ are each independently selected from the group consisting hydrogen, alkyls, aryls, substituted aryls, alkylaryls and arylalkyls; and $R_4$ and $R_6$ are each independently selected from the group consisting of H, alkyl, aryl, arylalkyl, a functional group having the formula —C(O)—, and substituted derivatives thereof, wherein the carbon to which $R_2$, Z and Y are bonded is chiral; and $R_5$, $R_6$, and $R_7$ taken together does not form —N(CH$_3$)$_2$.

29. A method according to claim 28 wherein Z is a functional group selected from the group consisting of benzyl, ethyl, isobutyl, n-propyl, (CH$_2$)$_4$NH$_2$, (CH$_2$)$_3$(C=NH)NH$_2$, and CH$_2$COOH.

30. A compound according to claim 28 wherein Y is a functional group selected from the group consisting of C(O)CF$_3$, C(O)CF$_2$C(O)OEt, C(O)$_2$-benzoxazole, C(O)$_2$-thiazole, C(O)oxadiazole, CH=CH(CO)OEt, CH=CHSO$_2$CH$_3$, CH=CHSO$_2$Ph, (CO)CH$_2$F, CHO, C(O)NHOH.

* * * * *